United States Patent [19]
Zaitsev

[11] Patent Number: 6,143,922
[45] Date of Patent: Nov. 7, 2000

[54] DIOLS AND UNSATURATED MONOMERS

[76] Inventor: Boris A. Zaitsev, Budapeshtskaya ul. 10, Bldg. 2, Apt. 157, St. Petersburg, 192242, Russian Federation

[21] Appl. No.: 09/167,923

[22] Filed: Oct. 7, 1998

[51] Int. Cl.[7] .................................................. C07C 69/017
[52] U.S. Cl. ........................................... 560/255; 568/635
[58] Field of Search .................................... 526/261, 265; 568/635; 560/254, 255

[56] References Cited

U.S. PATENT DOCUMENTS 5,763,688  6/1998  Ikariya et al. ........................... 568/814

FOREIGN PATENT DOCUMENTS 0849246  6/1998  European Pat. Off. ......... C07C 33/28

OTHER PUBLICATIONS

Zaitsev et al, J.Polym.Sci.,Part A: Polym.Chem.,34(7), 1165–81(Abstract enclosed to office action), 1996.
Zaitsev et al, Izv.Akad.NaukSSSR,Ser.Khim.,(8), 1881–3 (Abstract enclosed to office action), 1982.
Khramova, G.I., et al., "Joint Dehydration, Esterification, and Oligomerization of Unsaturated Secondary Aromatic Alcohols", *Journal of Applied Chemistry of the USSR*, 49(12), Consultants Bureau, New York, 2670–2675, (1976).
Lukasov, S.V., et al., "Correlation between the physicomechanical properties and structural parameters of rolivsan––type binders cured by thermal and catalytic methods", *Mechanics of Composite Materials*, 24(5), 573–579, (1988).
Lukasov, S.V., et al., "Structural Organization Of Chemically Modified Rolivsan MV–1 Cured By A Catalytic Method", *Mechanics of Composite Materials*, Consultants Bureau, New York, 363–367, (1992).
Yudin, V.E., et al., "Effect of Dissipative Properties of the Binder on the Process of Failure Carbon—Reinforced Plastics", *Mechanics of Composite Materiials*, 22(6), Consultants Bureau, New York, 706–712, (1986).
Zaitsev, B.A., et al., "Acid–Catalyzed Dimerization and Aralkylation in Divinylaromatic Compound—Aromatic Solvent System", *Bulletin of the Academy of Sciences of the USSR Division of Chemical Science*, 39(11), Consultants Bureau, New York, 2323–2330, (1990).
Zaitsev, B.A., et al., "Acid–Catalyzed Reactions of a Disecondary Aromatic Diol with Alkanols", *Institute of Macromolecular Compounds, Academy of Sciences of the USSR*, Plenum Publishing Corporation, 75–80, (1986).
Zaitsev, B.A., et al., "Cleavage of 4,4'—Bis (1–Acetoxyethyl) Diphenyl Ether", *Bulletin of the Academy of Sciences of the USSR Division of Chemical Science*, 31(8), Consultants Bureau, New York, 1672–1674, (1982).
Zaitsev, B.A., et al., "Condensation telomers of bisecondary aromatic glycols and carboxylic acids", *Polymer Science U.S.S.R.*, 25 (5), Pergamon Press, 2833–2840, (1983).
Zaitsev, B.A., et al., "Epoxy–Rolivsan Composites—Thermally Stable Binders For Reinforced Plastics", *Mechanics of Composite Materials*, 24 (5), Consultants Bureau, New York, 517–524, (1987).

Zaitsev, B.A., et al., "Epoxy–Rolivsan Compositions—Heat–Resistant Binders For Reinforced Plastics", *Mechanics of Composite Materials*, 22 (4), Consultants Bureau, New York, 404–407, (1986).
Zaitsev, B.A., et al., "Heat–resistant polymer composite Rolivsan MV–1", *Plastics Manuf.*, 96, 33, (1982).
Zaitsev, B.A., et al., "Kinetics of Homopolycondensation of a Bisecondary Aromatic Glycol in the Presence of an Acidic Catalyst", *Polymer Science Institute, U.S.S.R. Academy of Sciences*, 25(5), Pergamon Press, 1246–1253, (1983).

(List continued on next page.)

*Primary Examiner*—Sreeni Padmanabhan
*Attorney, Agent, or Firm*—Mark A. Litman & Assoc.

[57] ABSTRACT

The present invention relates to a novel composition of diols, said composition of diols comprising $$HO-(H_3C)R^4C-Q-CR^5(CH_3)-OH$$

wherein Q is a diaryl group comprising two aryl groups linked together directly (as in biphenyl) or bridged by an oxygen atom, sulfur atom or methyl group, $R^4$ and $R^5$ are independently selected from the group consisting of hydrogen and lower alkyl groups (e.g., methyl, ethyl, propyl and butyl, most preferably methyl). The diols will usually be provided as compositions which comprise either:

a solution of the diols, with the diols comprising more than 99% by weight solids of the solution, and whichdiol has less than 1% by weight of impurity selected from the group consisting essentially of monoaryl hydroxy compounds, especially monoaryl monohydroxy compounds, and monoaryl dihydroxy compounds where only one hydroxy group is attached directly to the aryl ring. The present invention also relates to a method of providing the novel composition of diols, said method comprising the processes of:
1) providing a solution of diol having the formula $$HO-(H_3C)R^4C-Ar-Z-Ar-CR^5(CH_3)-OH, \text{ or}$$
$$HO-(H_3C)R^4C-Q-CR^5(CH_3)-OH \; HO-(H_3C)R^4C-Ph-O'Ph-CR^5(CH_3)'OH$$

wherein Q is as defined above, Z is a bond or —O—, —S—, or a methine group (such as —CH2— or CHR°—, where R° is a substituent group such as lower alkyl, alkoxy, halogen, or the like), Ar is an aromatic group, especially a mono-ring aromatic groups, nd especially phenyl groups, and $R^4$ and $R^5$ are independently selected from the group consisting of hydrogen and lower alkyl groups (e.g., methyl, ethyl, propyl and butyl), said solution also comprising impurities selected from the group consisting of the monoaryl hydroxy groups (as defined herein);

removing at least some of said monoaryl hydroxy impurities which comprise monoaryl phenolic compounds.

22 Claims, No Drawings

OTHER PUBLICATIONS

Zaitsev, B.A., et al., "Linear Unsaturated bis–(4–Vinylphenyl) Ether Polymers", *Polymer Science USSR*, 26(8), Pergamon Press, 1789–1797, (1984).

Zaitsev, B.A., et al., "Mechanism and kinetics of the formation of linear unsaturated polymers of divinyl aromatics", *Acta Polymerica*, 34, 616–622, (1983).

Zaitsev, B.A., et al., "On the Mechanism of Formation of Oligomers based on Secondary Aliphatic–Aromatic Diols", *High Polymer Institute, U.S.S.R. Academy of Sciences*, 23 (8), Pergamon Press Ltd., 1957–1965, (1981).

Zaitsev, B.A., et al., "Proton–Transfer Polyaddition Reactions in Syntheses of Linear, Branched and Functionalized Poly (p–divinyl aromatics)", *Journal of Polymer Science*, 34, 1165–1181, (1996).

Zaitsev, B.A., et al., "Rolivsans—New Binders for Heat–Resistant and Strong Reinforced Plastics", *Mechanics of Composite Materials*, 18 (5), Consultants Bureau, New York, 512–515, (1982).

Zaitsev, B.A., et al., "Structure and Properties of Rolivans, Hardened by Thermal and Catalytic Methods", *Mechanics of Composite Materials*, 24 (4), Consultants Bureau, New York, 427–431, (1988).

Zaitsev, B.A., et al., "Synthesis of DI–and Polyatomic Secondary Aromatic Alcohols and Unsaturated Oligomers based on them", *Journal of Applied Chemistry of the USSR*, 50 (2), Consultants Bureau, New York, 389–392, (1977).

Zaitsev, B.A., et al., "Synthesis, structure and properties of poly[bis–(4–vinylphenyl) ether]", *Acta Polymerica*, 36 (10), 521–526, (1985).

Zaitsev, B.A., et al., "Thermal and Catalytic Cleavage of 4,4'—DI (1–Ethoxyethyl) Diphenyl Ether", *Bulletin of the Academy of Sciences of the USSR, Division of Chemical Science*, 32 (4), Consultants Bureau, New York, p. 870, (1983).

Zaitsev, B.A., et al., "Transformations of Disecondary Aromatic Glycols and Secondary Aromatic Alcohols in the Presence of Acidic Catalysts", *Journal of Organic Chemistry of the USSR*, 19 (11), Consultants Bureau, New York, 2043–2052, (1983).

DIOLS AND UNSATURATED MONOMERS

BACKGROUND OF THE INVENTION

1. Field of the Invention

The present invention relates to novel diol compositions, novel unsaturated monomers, novel resins, novel crosslinked polymers, novel polyester polymers, novel polyester polymers that display improvement over Rolivsan Resins, and to novel methods for obtaining the diols, unsaturated monomers, resins, and polymers.

2. Background of the Art

Polymers have been able to provide a wide range of properties and capabilities which have found tremendous outlet in the commercial markets. Polymers are used in all forms of technology from medicine, commercial and residential construction, vehicular construction, optics, imaging, protective coatings, film supports and sheeting, data storage and magnetic recording, toys, inks, adhesives, binders, structural housing for appliances and conveniences, and many other commercial areas. Each of these different fields has its own unique requirements for the performance of the polymeric materials. No one polymer can meet all of the requirements for all of the fields of potential use. For this reason, certain polymers have been developed to provide better performance within certain areas of technology. For example, polyesters (such as polyethyleneterephthalate and polyethylenenaphthalate) are preferred films supports for imaging technology, as are certain cellulose acetates. Polycarbonates are preferred polymeric materials for use with window construction and lens construction. Polyacrylates have found general utility for protective coatings, particularly weatherable and UV exposed protective coatings. Epoxy resins and acrylates have found wide acceptance as adhesive materials; silicone resins have found utility as caulking, release compositions, and moisture protective coatings and compositions. Polyamides have found utility as fabric materials, thermal adhesive and biocompatible polymers in the medical field, etc.

Even within these classes of polymers and these fields, variations in the properties of the polymer are important. Failure to understand the nature of the polymer, the actual reaction mechanisms in its polymerization, impurities and additives, reaction conditions and catalysis has led to the underutilization, underachievement or at least underappreciation of some polymer compositions.

In the 1970's and 1980's, a new class of polymer was introduced by research done in the Union of Soviet Socialist Republics by Dr. Boris A. Zaitsev at the Russian Academy of Sciences. This new class of resins was referred to in the literature as Rolivsan Resins. The resins originally were known to comprise at least about three ingredients comprising three monomers. Further advances in the resins provided for the inclusion of oligomers with the monomers. The resins were initially described as derived from compositions of monomers (M) comprising from about 1–45% by weight of:

$$p\text{-}(CH_2=CH-C_6H_4)_2O, \text{ bis-(4-vinylphenyl)ether} \qquad (M1 \text{ type})$$

2–35% by weight of:

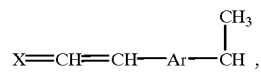

methacrylic ester of 4-vinyl-4'-(1-hydroxyethyl)-diphenyloxide or methacrylic ester of 4-vinyl-4'-(sec-ethylol)-diphenyloxide, and 5–30% by weight of:

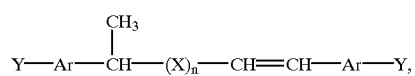

dimethacrylic ester of bis-[4-(1-hydroxyethyl)phenyl]ether, and

5–88% by weight of:

oligomers.

The oligomers which were also described in the literature as possibly being present within the compositions (resulted from acid-catalyzed repeated dimerization and co-dimerization reactions of M1 with itself and M2) were described as having different formulae, e.g.:

$$Y-Ar-\overset{\overset{\displaystyle CH_3}{|}}{CH}-(X)_n-CH=CH-Ar-Y,$$

wherein R=H, —CH$_3$ and $$Y=CR=CH_2, \text{ or } -CH(CH_3)OCOC(CH_3)=CH_2,$$

and $$X=CH=CH-Ar-\overset{\overset{\displaystyle CH_3}{|}}{CH},$$

or a fused ring system (arylindan), and

Ar=C$_6$H$_4$—O—C$_6$H$_4$, and n=0–3

The objective of this class of resins was to provide easy processing for high temperature resistant thermosetting resins and advanced composites. The resin reaction mixtures were provided as solvent-free compositions having viscosity ranges of from 600 up to 5,000 cps at room temperature, with melting points between 5 and 50° C. for the uncured resins. The resins were to provide excellent chemical resistance to the most aggressive chemical materials (e.g., organic solvents, strong acids, alkalis, hydrazine and solutions of hydrofluoric acid). The resins were also to provide high-temperature (300±50° C.) performance properties and advanced composite reinforced plastics (e.g., fiberglass, polyamide and polyimide fiber, graphite, and tungsten—reinforced plastics). The resins were also to have mixing compatibility with conventional reactive resins and oligomers such as epoxy resins, unsaturated polyester resins, vinylester resins, and bis-maleimide resins. The Rolivsan Resins were also expected to exotherm in the presence of phenols, condensing with them quite readily (alkylating phenols by ethylenically unsaturated ingredients of Rolivsan Resins) at room temperature in the presence of acidic catalysts (strong acids).

An essential precursor for obtaining Rolivsan resins was bis-[4-(1-hydroxyethyl)phenyl] ether (referred to as BHEPE). The BHEPE had been obtained by the catalytic hydrogenation of bis-(4-acetyl)phenyl ether (BAPE), for example on a Raney-Nickel catalyst at conditions varying from room temperature (at high pressure) to 40 to 50° C. with a hydrogen pressure of 100 atmospheres for 0.5 to 1 hour in ethyl alcohol followed by recrystallization from toluene or benzene (mp 86° C.).

The Rolivsan Resins were formed by heating the BHEPE (which have been found by the present inventors to have comprised uncontrollable amounts (~5±3%) of a phenolic impurity) with unsaturated carboxylic acids (e.g., methacrylic acid) in the presence of the considerable amounts (2.5% of BHEPE weight) of acid catalysts (such as p-toluenesulfonic acid monohydrate) in an aromatic solvent at its boiling temperature in the presence of considerable amounts (>1% of BHEPE weight) of hydroquinone. It has been found by Applicant in the background of the present invention that the synthetic procedure for the production of intermediates (precursors) for the resins, especially in the synthesis of the diols which are then converted to the ethylenically unsaturated monomeric and oligomeric components of the resin, formed by-product impurities. These impurities have been found by the present inventors to produce heretofore unknown active effects on the properties and performance of the resulting resin and prevent the diols and their polymerizably active products of their transformations from use in other fields where purity might be even more critical. Some of these impurities were carried through to the final resin composition, even where standard purification techniques were used, because the physical properties of the impurities did not substantially differentiate the properties of the objective compounds.

According to the method for the manufacture of BHEPE, the basis of the pilot scale production of bis-[4-(1-hydroxyethyl)phenyl] ether (BHEPE) was by hydrogenation of bis-(4-acetyl)phenyl ether (BAPE) in the presence of Raney-nickel catalyst in processes exemplified by the following description (with variations in temperatures and pressures and time as noted herein): in Examples 1–6, in the section of EXAMPLES below.

These examples illustrate that the previously published and commercially used procedures had operated with quite high concentrations of acidic catalyst (p-toluenesulfonic acid) (2.5 to 28% of BHEPE weight) and hydroquinone (1 to 2% of BHEPE weight), and the products retained an extra-amount of the phenolic compounds as unremoved impurities in the BHEPE.

As a result, according to the Soviet Union technical (standard) specifications for the Rolivsan MV-1 resin manufacture (TU-6-14-24-62-79, valid from Jul. 20, 1979 for one ton production, and, more recently, TU 6-36-57-0-91 (instead of the previous TU-6-14-24-143-85) from Feb. 15, 1991 to Feb. 15, 1994) (Zaitsev, B. A. et al., Rolivsans—New Binders for Heat-Resistant and Strong Reinforced Plastics, *Mechanics of Composite Materials,* 18(5):512–515 (1982); Zaitsev, B. A. et al., Heat stable Polymer Material Rolivsan MV-1, *Plast. Massy,* 2:12–13 (1981)), the physical properties of uncured resin and mechanical characteristics of materials (glass fiber cloth laminates) could be uncontrollably changed in the following extremely wide range:
Viscosity at 25° C.: 450 to 5,000 cps
Refractive index, $n_D^{20}$: 1.560 to 1.610
Flexural strength for glass fiber cloth laminates prepared on the basis of Rolivsan resin at 20° C.:
420 to 670 Mpa It can be seen that Rolivsan resins have not provided the low range of viscosity and the intended viscosity (less than 300 cps at 25° C., especially less than 200 at 25° C., or about 100 cps at RT) that was very important for some uses, such as polymer coatings, filled polymer compositions, reactive diluents, crosslinking agents, impregnating and sealing compounds, etc. This drawback has been due to high extent of generalization of the previously proposed method for the synthesis of resins that did not provide the controllable ratio of monomeric esters and (di)vinylaromatic monomers to unsaturated oligomers, the intended structure, amount (content), and molecular weight (and molecular weight distribution) of oligomeric component. The needed characteristics are provided with a number of proper (differentiating) methods of the present invention for obtaining novel resins having various compositions with a quite controllable, more narrow intended parameters and properties.

Another disadvantage of Rolivsan resins and their method of preparation is related to their very low and uncontrollable reactivity in three dimensional free radical (co)polymerizations as the most usable method for the cure of unsaturated monomers and oligomers. It can be seen from technical specifications that their gelation time was very long (0.5 to 1.5 hr at 140–150° C.). It implies that only high temperature cure schedules could be applied for preparing polymer materials and composites.

Another disadvantage of the prior method for obtaining Rolivsan resins and related resins was in underestimating and not comprehending the effect of the acidic catalyst nature, its concentration and temperature-time schedule in the resin synthesis on structure and amount of the forming oligomeric component, and the composition of the resin on the whole.

These drawbacks had strongly limited the scope of applications of Rolivsan resins and related resins. The main reason for this behavior and properties was in the disadvantage of the method developed for their preparation. The method did not also take into account of occurring the alkylation reaction between unsaturated components (formed in the course of the resin's synthesis) and phenolic compounds both placed in the initial reaction mixture specifically as inhibitors (e.g., hydroquinone) for preventing thermal polymerization of monomers and oligomers, and being carried through the reaction along with the main reactant (BHEPE). These comprised the above-mentioned inconspicuous and unremoved diol impurities (in part resulting from a side-reaction of hydrogenolysis during the hydrogenation of BAPE for BHEPE synthesis).

BRIEF DESCRIPTION OF THE INVENTION

The present invention relates to a novel composition of diols, said composition of diols comprising

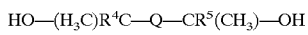

wherein Q is an at least diaryl group comprising two aryl groups linked directly together or bridged by an oxygen atom, sulfur atom or alkyl group, preferably an oxygen or methyl group,
$R^4$ and $R^5$ are independently selected from the group consisting of hydrogen and lower alkyl groups (e.g., methyl, ethyl, propyl and butyl, most preferably methyl). The diols will usually be provided as compositions that comprise either:
a solution of the diols, with the diols comprising more than 99% by weight of the solids of the solution, and
diol which has less than 1% by weight of impurity selected from the group consisting essentially of monoaryl hydroxy (Ar—OH) or sulfhydryl (Ar—SH) compounds, especially monoaryl monohydroxy or monosulfhydryl compounds, and monoaryl dihydroxy or hydroxy-sulfhydryl compounds where only one hydroxy or sulfhydryl group is attached directly to the aryl ring.

The present invention also relates to a method of providing the novel composition of diols, said method comprising the processes of:

1) providing a solution comprising at least one diol having the formula

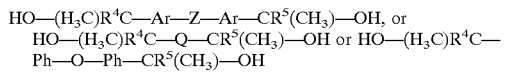

HO—(H$_3$C)R$^4$C—Ar—Z—Ar—CR$^5$(CH$_3$)—OH, or
HO—(H$_3$C)R$^4$C—Q—CR$^5$(CH$_3$)—OH or HO—(H$_3$C)R$^4$C—Ph—O—Ph—CR$^5$(CH$_3$)—OH wherein Q is as defined above, Z is —O—, —S—, or a methine group (such as —CH$_2$— or CHR$^O$—, where R$^O$ is a substituent group such as lower alkyl (C1 to C4), alkoxy (C1–C4) group, phenyl group, halogen, or the like), Ar is an aromatic group (e.g., phenyl, naphthyl, furyl and the like), especially mono-ring aromatic groups, and especially phenyl groups, and R$^4$ and R$^5$ are independently selected from the group consisting of hydrogen and lower alkyl groups (e.g., methyl, ethyl, propyl and butyl group), said solution also comprising impurities selected from the group consisting of the monoaryl hydroxy groups (as defined herein);

removing at least some of said monoaryl hydroxy or sulfhydryl (mercaptan) impurities which comprise monoaryl phenolic or thiophenolic compounds.

A simple purification method according to the present invention comprises dissolving the diol with monoaryl phenolic or thiophenolic impurities in a solvent (e.g., low alkyl alcohol such as methanol, ethanol and propanol), adding a basic compound to the mixture to form a salt of the monoaryl phenolic or thiophenolic compound, and then separating a main liquor from a solution or precipitate of the diol, thereby reducing the concentration of monoaryl phenolic or thiophenolic compound in the diol precipitate. The monoaryl, monohydroxy, non-phenolic compound may be separated by recrystallization in solvent, such as toluene.

The present invention also relates to novel unsaturated monomers. These monomers may be made from the diols of the present invention. The monomers may have central nuclei comprising divinylaromatic monomer selected from the group consisting of

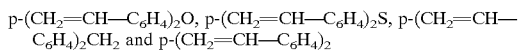

p-(CH$_2$=CH—C$_6$H$_4$)$_2$O, p-(CH$_2$=CH—C$_6$H$_4$)$_2$S, p-(CH$_2$=CH—C$_6$H$_4$)$_2$CH$_2$ and p-(CH$_2$=CH—C$_6$H$_4$)$_2$ with optional substitution on the compounds, especially the phenyl rings (C$_6$H$_4$).

The present invention also relates to novel diols, unsaturated compounds and resin compositions with reduced amounts of monoaryl phenolic or thiophenolic impurities therein, for example, as an adduct with M1, M2, and oligomer, methods of curing the resins (especially under conditions which were not amenable to curing with resins containing adducts of monoaryl phenolic impurities), and polymeric compositions containing novel classes of copolymerizable monomers with the novel resins.

DETAILED DESCRIPTION OF THE INVENTION

The present invention relates to a novel composition of diols, a novel process for the synthesis of the diols, diethylenically unsaturated monomers synthesized from the diols, resins containing those diethylenically unsaturated monomers, oligomers, and polymer compositions formed by polymerization of those resin compositions.

The novel composition of diols comprises:

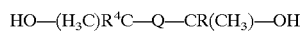

HO—(H$_3$C)R$^4$C—Q—CR(CH$_3$)—OH wherein Q is a diaryl group comprising two, three, four, five, six and more aryl groups linked directly as in biphenyl, or bridged by oxygen atoms or sulfur atoms, such as Ph(OPh)$_n$Ph, or Ph(SPh)$_n$Ph.
R$^4$ and R$^5$ are independently selected from the group consisting of hydrogen and lower alkyl groups (e.g., methyl, ethyl, propyl and butyl, most preferably hydrogen, so that the terminal -ol group is

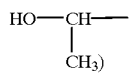

HO—CH—
    |
    CH$_3$)

wherein the diols comprise either:
a solution of the diols, with the diols comprising more than 99% by weight dissolved material or solids of the solution, and
any other diol composition which comprises less than 1% by weight of impurity selected from the group consisting essentially of monoaryl hydroxy compounds, especially monoaryl monohydroxy compounds, monoaryl phenolic or thiophenolic compounds, and monoaryl dihydroxy or hydroxy-sulfhydryl compounds where only one hydroxy or sulfhydryl group is attached directly to the aryl ring.

The present invention also relates to a method of providing the novel composition of diols, said method comprising the processes of:

providing a solution of diol having the formula

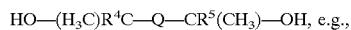

HO—(H$_3$C)R$^4$C—Q—CR$^5$(CH$_3$)—OH, e.g.,

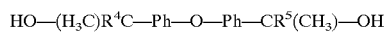

HO—(H$_3$C)R$^4$C—Ph—O—Ph—CR$^5$(CH$_3$)—OH wherein Q is as defined above and R$^4$ and R$^5$ are independently selected from the group consisting of hydrogen and lower alkyl groups (e.g., methyl, ethyl, propyl and butyl), most preferably hydrogen,
said solution also comprising impurities selected from the group consisting of the monoaryl hydroxy groups;

2) removing at least some of said impurities which comprise monoaryl, phenolic or thiophenolic compounds. A simple purification method comprises dissolving the diol Or diol with monoaryl phenolic or thiophenolic impurities in a solvent (e.g., low alkyl alcohol such as methanol, ethanol and propanol), adding a base or base-releasing compound to the mixture to form a salt of the monoaryl phenolic or thiophenolic compound (e.g., a phenolate salt), precipitating the diol in water or ethanol (or other convenient differentiating solvent system) and then separating a main liquor from the solution or liquor carrying the precipitate of the diol, thereby reducing the concentration of monoaryl phenolic or thiophenolic compound in the diol precipitate. The monoaryl, monohydroxy, non-phenolic compound may be separated by recrystallization in solvent, such as toluene, leaving in the case of the most preferred diol, para-HO—(H$_3$C)HC—Ph—O—Ph—CH(CH$_3$)—OH, a purer diol. It is particularly desirable to remove at least 10% by weight of all monoaryl impurities (either total or with respect to a single species, e.g., the monoaryl hydroxy compounds), preferably at least 25 or 30% by weight of monoaryl phenolic or thiophenolic compounds, more preferably at least 50 or 60% by weight, still more preferably at least 75, 80 or 90% by weight, and most preferably at least 95 to 99% up to 100% by weight of the monoaryl phenolic or thiophenolic impurities.

The invention also describes a process for the synthesis of the diol by hydrogenation of a corresponding diketone under conditions of catalysis, temperature, time and pressure which avoids the substantive formation of monoaryl hydroxy or mercaptan impurities.

The products of the by-reaction of the hydrogenolysis step of converting the diketone intermediate:

O=(H$_3$C)R$^4$C—Q—CR$^5$(CH$_3$)=O, or more clearly configured as

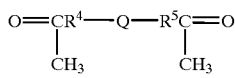

wherein Q is as defined above,
into the diol (e.g., caused by the splitting or cleaving of BHEPE at the oxygen bridging group between the two aryl groups) are of the general X—Ar—X type (e.g., where each X independently represents H, OH or a group containing an OH moiety), particularly where the products are the H—Ar—OH or HO—Ar—OH hydrogenolysis product formed after cleavage of the oxide link as in BHEPE. The cleavage produces a compound with an unsatisfied oxygen or sulfur which is hydrogenated to form the phenol or thiophenol group, and an unsatisfied ring carbon atom which is hydrogenated to complete the phenyl ring. These compounds also include the H—Ar—R$^3$—OH and HO—Ar—R$^3$—OH type compounds such as:

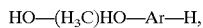

para-HO—Ar—CH(CH$_3$)—OH, or para-HO—Ar—CH(CH$_3$)—OH, more particularly described for the preferred diol as

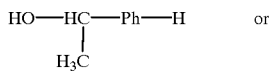

and

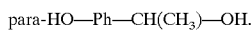

R$^3$ in this circumstance is a branched alkyl linkage, preferably of 2 to ten carbon atoms, more preferably 2 to six carbon atoms, and most preferably 2 to 3 carbon atoms. Ar is generally a monoaryl group, such as phenyl and substituted phenyl, and in certain circumstances may lead to a trifunctional group which will assist in providing a more highly crosslinked product, where Ar is HO—(H$_3$C)HC—Ph—, or is HO—(H$_3$C)HO—Ar$^2$, wherein Ar$^2$ is also an aryl group such as phenyl, although further presence of additional hydroxyl containing groups on Ar$^2$ is not likely or desirable from a selection of initial reactants. It is these materials which are the primary adverse by-products in the original Rolivsan resins. These materials may be generically described, for example, as mono-aryl hydroxy compounds. Monoaryl hydroxy compounds are defined as low molecular weight (less than 300, preferably less than 200, more preferably less than 150) compounds having a single aromatic ring (preferably or usually phenyl) and at least one hydroxy group, attached to the aromatic ring itself (an arylol, such as phenol) or as a terminal substituent on a substituent group (e.g., sec-ethylol). The term monaryl phenolic compound includes all phenol or phenolic compounds having a single phenyl group and one or more (especially one) hydroxy groups directly bonded onto the phenyl ring. The term monoaryl arylol is the generic equivalent for the term monoaryl phenol.

Thus, the earlier undetected, non-identified and unremoved by-products of the reduction of the diketones, BAPE's reduction (hydrogenation) included methyl benzyl alcohol (H—Ph—CH(CH$_3$)—OH) and para-hydroxy methyl benzyl alcohol (para-HO—(H$_3$C)HC—Ph—OH), and the like, where Ph is phenyl (—C$_6$H$_4$—). These compounds greatly affected the reaction of the synthesis, structure, composition, the polymerization, and physical properties of the resin, were uncontrollable (and not appreciated or known to exist in the compositions), and both impurities were neither recognized as present, nor intentionally removed during the normal purification process used on the resin precursors. During some production runs of the Rolivsan resins, the diols were recrystallized from toluene or benzene which would have removed some of the monoaryl hydroxy compounds (only the non-phenolic compounds), that is those which did not form phenols during cleavage. The phenol compounds formed during cleavage were not known to be removed before the resin's synthesis.

The solution of diol may also be provided by a synthetic procedural route which differs from the prior art process. The new synthetic procedural route comprises the steps of hydrogenating the ketone precursor for the diol with a more efficient catalyst for the heterogeneous catalysis hydrogenation reaction than the Raney-nickel (inclusive of Raney-nickel/titanium) catalysts used in the prior art. This process would include the hydrogenation of the diacetyl (diketone) precursors of the diols, such as bis-(4-acetyl)phenyl ether (BAPE) in the presence of the hydrogenation catalyst, such as, for example, platinum based catalysts (e.g., platinum carried on alumina), palladium based catalysts (e.g., palladium carried on alumina), lithium-aluminum based catalysts (e.g., lithium-aluminum hydride), borohydride catalysts (e.g., sodium borohydride), etc. These classes of catalysts are well known, and only upon identification by the inventor of the need for selection of catalysts with better conversion properties of the diketones to the diols, could the selection of appropriate catalysts from the known classes by one of ordinary skill in the art be readily made. Not only may the catalyst change reduce the level of impurity of the monoaryl hydroxy type in the composition, but the reaction time and reaction conditions may be moderated and a more pure product still produced. For example, the prior art synthesis of the Rolivsan resins used reaction conditions of from about 40 to 100 atmospheres during the hydrogenation of the diketones and temperatures of from room temperature to 40 or 50° C. The room temperature was used with the higher pressures so that there were not believed to be described conditions of room temperature cure at less than 60 atmospheres. Then use of hydrogenation catalysts other than (or in addition to) the Raney-nickel catalysts also allows the use of room temperature to less than 30° C., at pressures below 40 atmospheres, preferably below 30 atmospheres, and most preferably below 20, below 15 and below 10 atmospheres. Even with these less forceful conditions, the use of alternative catalysts reduces the time of the reaction and the purity of the product with respect to the absence (e.g., less than 1% by weight of diols, preferably less than 0.75% by weight, and more preferably less than 0.5% or less than 0.3% by weight of diols) of monoaryl hydroxy compounds.

Novel ethylenically unsaturated monomer-oligomer compositions may be synthesized from these novel diol compositions or the pure diols. The ethylenically unsaturated monomer may be synthesized from the pure diol or novel diol composition obtained by hydrogenation of a diketone at temperatures below 30° C. and pressures below 40 atmospheres.

Having now described the novel diols, having an absence or reduced amount of monoaryl hydroxy or sulfhydryl substituted compounds, the novel ethylenically unsaturated monomers having an absence or reduced amount of monoaryl hydroxy substituted compounds alkylated by ethylenically unsaturated resin components, the novel resin compositions of the invention may be described. These novel vinyl ester resin compositions which may be later polymerized comprise at least the following four components:

2–95% by weight of:
  diaryl compounds comprising at least two aryl groups linked directly together (as in biphenyl) or bridged by a linking group, each of said at least two aryl groups having a vinyl group attached thereto, such as all p-(CH$_2$=CH—Ar)$_2$O, p-(CH$_2$=CH—Ar)$_2$S, p-(CH$_2$=CH—Ar)$_2$CH$_2$, p, p'-CH$_2$=CH—Ar—Ar—CH=CH$_2$ p-(CH$_2$=CH—C$_6$H$_4$)$_2$O, bis-(4-vinylphenyl) ether (or its counterparts where the ether linkage is replaced with sulfur or methine group or phenyl rings are linked directly), 2–65% by weight of:
  a methacrylic acid ester of a vinyl-substituted sec-ethyloldiaryl oxide or its thioether or methine or biphenyl counterpart, e.g., CH$_2$=CH—Ar—O—Ar—CH(CH$_3$)OCOC(CH$_3$)=CH$_2$ 4-vinyl-4'-(1-hydroxyethyl)-diphenyl-oxide or methacrylic ester of 4-vinyl-4'-(sec-ethylol)-diphenyloxide (or its counterparts where the ether linkage is replaced with sulfur or methine group) or bridging atom (or group) is absent, i.e., the rings are linked together directly), and 1–35% by weight of:
  dimethacrylic acid esters of bis-[4-(1-hydroxyethyl)aryl] ether, thioether or methine, e.g., (p—CH$_2$=C(CH$_3$)—COOCH(CH$_3$)Ar)$_2$O dimethacrylic acid esters of bis-[4-(1-hydroxyethyl) phenyl] ether (or its counterparts where the ether linkage is replaced with sulfur, methyne group), or aromatic rings are linked together directly), and 2–95% by weight of:
  unsaturated oligomers which can be described mainly by the formulae:

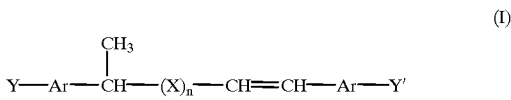

and/or

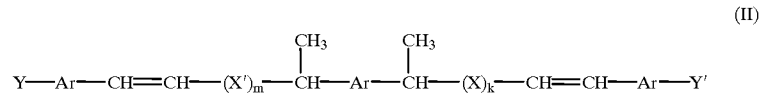

wherein Ar is as defined above, and additionally including also diaryl species as those selected from biphenyl, diphenyl methane, 1,1-diphenyl ethane, naphthalene, diphenyl ether, diphenyl sulfide (where the thioether counterpart was used), diphenyl sulfone, 2,2-diphenyl propane, 1,3-diphenoxybenzene, 1,4-diphenoxybenzene, bis-(4-phenoxyphenyl) ether, bis-(3-phenoxyphenyl) sulfide, 4-phenoxy biphenyl, 1,4-dibenzyl benzene, 1,3-dibenzyl benzene, 3-phenyl biphenyl, and the like, or alkylated aryl species comprising one, two, three or more alkyl groups comprising C$_1$ to C$_{15}$, and X=CH(CH$_3$)—Ar—CH=CH, X'=CH=CH—Ar—CH(CH$_3$), Y=Y'=CH$_2$=CH, CH$_2$=CR—COO—CH(CH$_3$), or Y=CH$_2$=CH, Y'=CH$_2$=CR—COO—CH(CH$_3$), R=H, CH$_3$, alkyl (C$_1$ to C$_{15}$), n=0–3, m=k=0, or m=1 and k=0, or m=0 and k=1, or m=k=1.

The important feature of a composition is structure, content (ratio), and molecular weight of the components. Main components of the composition (resin) are unsaturated oligomers formed by a series of consecutive acid-catalyzed dimerization reactions or actions with participation of CH$_2$=CH—Ar— endgroups. The method for obtaining ethylenically unsaturated compositions described in previous inventions have not taken into account that the structure, molecular weight and properties of the oligomers are very sensitive to the nature and concentration of acidic catalyst, and temperature of the process that usually depended on the boiling temperature of the solvent used. Thus, this new invention shows that the oligomers with high level of unsaturation and higher molecular weight are formed in the case of application of such an acidic catalyst as p-toluenesulfonic acid (TSA) used in a relatively considerable amount (greater than 2, greater than 3 or greater than 5 mmole/L, preferably 5–20 or 30 mmole/L, and more preferably about 10–15 mmole/L) and in a temperature range of about 30–100° C., preferably 40–90° C., more preferably 50–85° C., and still more preferably about 70–80° C.

Therefore, a general method of synthesizing the polymerizable composition with a wide range of ingredients comprising the steps providing of a series of transformations of the diol of the invention with a carboxylic acid wherein heating the diols (D) with said carboxylic acid, preferably with methacrylic acid (A) is performed at mole ratio D:CA (MAA) not less than 1:0.1, preferably 1:1.5–2.5, or more in the presence of relatively the lowest concentration of an acid catalyst, preferably a sulfonic acid compound, such as p-toluenesulfonic acid (monohydrate) (TSA) (mainly 0.9–14.0 mmole/L), preferably 3.0–7.0 mmole/L) in aromatic solvent, preferably in toluene at the boiling temperature (80–160° C.) of the reaction mixture, preferably at 100–120, more preferably ~103–110° C. while removing the reaction water evolving during the resin's synthesis and with successive stirring at 70–80° C. in the presence or the absence of any extra-amount of acidic catalyst (the special oligomerization stage) aimed at formation of more amount and higher molecular weight of ethylenically unsaturated oligomers that may be described form formula (I) or (II).

However, in the presence of sulfo-cationite (ion-exchange resin, e.g., Amberlite IPR-69 ion-exchange resin, sulfonic acid functionality (strongly acidic), capacity 5 meq/g (dry) or Amberlyst XN-1010 ion-exchange resin, strongly acidic, macroreticular, high surface-area suitable for non-aqueous applications (see, e.g., Aldrich Catalog), or "KU-23" (Russian trade name for ion-exchange resin), the unsaturated oligomers of the above type, which could be described by formula (I) or (II), are not practically formed. Instead of them, the oligomers of another type are formed, which could be described by formula (III):

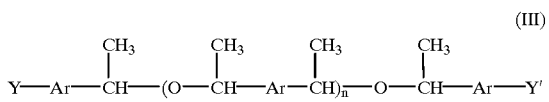

wherein Y, Y', Ar, and n are as defined for in formula (I). The IR spectrum of the oligomer component exhibits the absorption band of ether (—Ar—(CH(CH$_3$)—O—CH(CH$_3$)—Ar) group (at 1100 cm$^{-1}$) rather than unsaturated trans- (—CH=CH—) group (965 cm$^{-1}$) characteristic of unsaturated oligomers described by the formula (I) or (II). $^1$H-NMR spectrum of the oligomer component of the composition exhibits characteristic signals: two overlapping doublets at δ 1.3 ppm (for methyl groups of the ether unit [—CH(CH$_3$)—O—CH(CH$_3$)—]) and two overlapping quadruplets at δ 4.2 ppm (for methyne group of this ether unit).

Consequently, in the previous inventions/patents, the method for obtaining the resins had not permitted controlling its above-mentioned parameters and characteristics of the compositions.

Taking into consideration the need of attaining control of the structure-composition-properties and the requirements of the various fields of use, the claimed compositions of the invention with very wide range of components may be subdivided into four specific compositions with the narrower range of the components and properties, and specific methods for their preparation:

1. Vinyl ester compositions with the lowest viscosity (80 to 600 cps at RT), an increased content of ester endgroups (ester number 160 to 190 mg KOH/1 g of the product and higher), i.e., said compositions with increased content of monomeric and oligomeric esters, and impoverished compositions with vinyl and divinyl aromatic groups (in monomers and oligomers comprising mainly dimers, trace of trimers and tetramers) [examples 7–14, 15 (sample 1), 16 (sample 1), 17 (sample 1), 18–20 comprising:
5–45% by weight of:
  diaryl compounds comprising at least two aryl groups linked directly together (as in biphenyl) or bridged by a linking group, each of said at least two aryl groups having a vinyl group attached thereto, such as
  p-(CH$_2$=CH—Ar)$_2$O, p-(CH$_2$=CH—Ar)$_2$S, p-(CH$_2$=CH—Ar)$_2$CH$_2$, p,p'-CH$_2$=CH—Ar—Ar—CH=CH$_2$ p-(CH$_2$=CH—Ar)$_2$O, bis-(4-vinylphenyl) ether (or its counterparts where the ether linkage is replaced with sulfur or methine group), and
10–65% by weight of:
  a methacrylic acid ester of a vinyl-substituted sec-ethyloldiaryl oxide or its thioether or methine or biphenyl counterpart, e.g.,

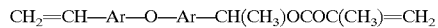

4-vinyl-4'-(1-hydroxyethyl)diphenyloxide or methacrylic ester of 4-vinyl-4'-(sec-ethylol) diphenyloxide (or its counterparts where the ether linkage is replaced with sulfur or methine group), or bridging atom (or group) is absent, i.e., the rings are linked together directly, and
5–35% by weight of:
  dimethacrylic acid esters of bis-[4-(1-hydroxyethyl)aryl] ether, thioether or methine, e.g.,

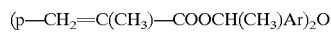

dimethacrylic acid esters of bis-[4-(1-hydroxyethyl) phenyl] ether (or its counterparts where the ether linkage is replaced with sulfur, methyne group), or aromatic rings are linked together directly, and
2–35% by weight of:
  unsaturated oligomers which can be described mainly by the formulae (I) and/or (II).

1.1 A method for obtaining these compositions is in heating the diols (D) with carboxylic acids (CA), preferably with methacrylic acid (MAA) (at mole ratio C:CA (MAA) not less than 1:1.1, preferably 1:1.5–2.5, or more) in the presence of relatively the lowest concentration of a sulfonic acid, such as p-toluenesulfonic acid (monohydrate) (TSA) (mainly 0.9–14.0 mmole/L), preferably 3.0–7.0 mmole/L in aromatic solvent, preferably in toluene at the boiling temperature of the reaction mixture, preferably at ~103–111° C. with removing the reaction water evolving during the resin's synthesis.

2. Vinyl ester compositions with increased molecular weight (increased viscosity) and impoverished with ester endgroups, i.e., rich with oligomers of higher molecular weight comprising [examples 25–31]:
5–30% by weight of:
  diaryl compounds comprising at least two aryl groups linked directly together (as in biphenyl) or bridged by a linking group, each of said at least two aryl groups having a vinyl group attached thereto, such as

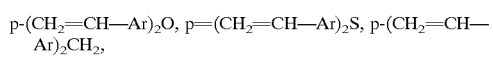

p-(CH$_2$=CH—Ar)$_2$O, bis-(4-vinylphenyl) ether (or its counterparts where the ether linkage is replaced with sulfur or methine group), and
10–20% by weight of:

a methacrylic acid ester of a vinyl-substituted sec-ethyloldiaryl oxide or its thioether or methine or biphenyl counterpart, e.g.,

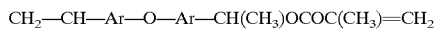

4-vinyl-4'-(1-hydroxyethyl)diphenyloxide or methacrylic ester of 4-vinyl-4'-(sec-ethylol) diphenyloxide (or its counterparts where the ether linkage is replaced with sulfur or methine group), or bridging atom (or group) is absent, i.e., the rings are linked together directly, and 1–30% or 10–30% by weight of:
dimethacrylic acid esters of bis-[4-(1-hydroxyethyl)aryl] ether, thioether or methine, e.g.,

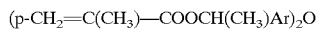

dimethacrylic acid esters of bis-[4-(1-hydroxyethyl) phenyl] ether (or its counterparts where the ether linkage is replaced with sulfur, methyne group), or aromatic rings are linked together directly, and 40–95% by weight of:
unsaturated oligomers which may be described mainly by the formulae (I) and/or (II): 2.1. A method for obtaining these compositions comprises heating the diols (D) with carboxylic acids (CA) in the presence of the relatively highest concentration of sulfonic acid, preferably TSA (greater than 2, greater than 3 or greater than 5 mmole/L, preferably 5–20 or 30 mmole/L, and more preferably about 10–15 mmole/L) in aromatic solvent, preferably benzene, or toluene or o-xylene at the boiling temperature of the solvent with removing the reaction water evolving during the condensation process. In the event of performing the resin's synthesis in toluene, o-xylene or other higher boiling aromatic solvents, after removing released water, the reaction mixture should be kept at 70–80° C. or lower for 1 or several hours with or without adding extra amounts of acidic catalyst (for occurrence of oligomerization on styrene-like endgroups of monomers M1 and M2, and ethylenically unsaturated oligomers (mainly dimers and trimers) described by formula (I) or (II)).

3. Vinyl ester compositions with low melt viscosity, increased content of vinyl (styrene-like) endgroups, and impoverished with ester endgroups, i.e., rich with vinyl and divinyl aromatic monomers and oligomers comprising [examples 25, 30, 31]:

15–60% by weight of:
diaryl compounds comprising at least two aryl groups linked directly together (as in biphenyl) or bridged by a linking group, each of said at least two aryl groups having a vinyl group attached thereto, such as

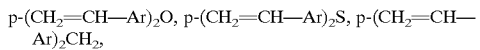

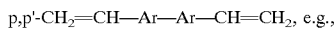

p-(CH$_2$=CH—Ar)$_2$O, bis-(4-vinylphenyl) ether (or its counterparts where the ether linkage is replaced with sulfur or methine group), and 10–20% by weight of:
a methacrylic acid ester of a vinyl-substituted sec-ethyloldiaryl oxide or its thioether or methine or biphenyl counterpart, e.g.,

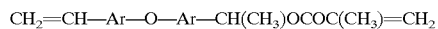

4-vinyl-4'-(1-hydroxyethyl)diphenyloxide or methacrylic ester of 4-vinyl-4'-(sec-ethylol) diphenyloxide (or its counterparts where the ether linkage is replaced with sulfur or methine group), or bridging atom (or group) is absent, i.e., the rings are linked together directly, and 2–30% by weight of:
dimethacrylic acid esters of bis-[4-(1-hydroxyethyl)aryl] ether, thioether or methine, e.g.,

dimethacrylic acid esters of bis-[4-(1-hydroxyethyl) phenyl] ether (or its counterparts where the ether linkage is replaced with sulfur, methyne group), or aromatic rings are linked together directly, and 10–40% by weight of:
unsaturated oligomers which may be described mainly by the formulae (I) and/or (II): 3.1 A method for obtaining these compositions comprises heating the diols (D) with carboxylic acids (CA) (with mole ratio D:CA not less than 1:0.5, preferably 1: 1, or more) in the presence of relatively the lowest concentration of sulfonic acid, preferably TSA (mainly 2–10 mmole/L) in aromatic solvent (avoiding benzene), preferably toluene or o-xylene, at the boiling temperature of the solvent, preferably 1 10–144° C. while removing the reaction water evolving during the condensation process.

4. Vinyl ester compositions with middle molecular weight (middle viscosity) having oligomers with units comprising (examples 32–36):

10–25% by weight of:
diaryl compounds comprising at least two aryl groups linked directly together (as in biphenyl) or bridged by a linking group, each of said at least two aryl groups having a vinyl group attached thereto, such as

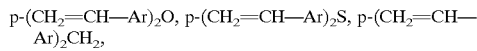

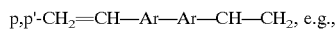

p-(CH$_2$=CH—Ar)$_2$O, bis-(4-vinylphenyl) ether (or its counterparts where the ether linkage is replaced with sulfur or methine group), or aromatic rings are linked together directly, and 10–25% by weight of:
a methacrylic acid ester of a vinyl-substituted sec-ethyloldiaryl oxide or its thioether or methine or biphenyl counterpart, e.g.,

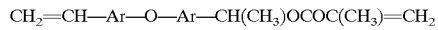

4-vinyl-4'-(1-hydroxyethyl)diphenyloxide or methacrylic ester of 4-vinyl-4'-(sec-ethylol) diphenyloxide (or its counterparts where the ether linkage is replaced with sulfur or methine group), or bridging atom (or group) is absent, i.e., the rings are linked together directly.

20–35% by weight of:
dimethacrylic acid esters of bis-[4-(1-hydroxyethyl)aryl] ether, thioether or methine, e.g.,

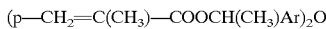

dimethacrylic acid esters of bis-[4-(1-hydroxyethyl) phenyl] ether (or its counterparts where the ether linkage is replaced with sulfur, methyne group), or aromatic rings are linked together directly, 20–50% by weight of:
unsaturated oligomers which may be described mainly by the formula (III):

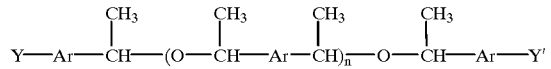

wherein Y, Y', Ar, and n are as defined for formula (I). The IR spectrum of the oligomer component exhibits the absorption band of ether (—Ar—(CH(CH$_3$)—O—CH(CH$_3$)— group (at 1100 cm$^{-1}$ rather than unsaturated trans- —CH=CH— group (965 cm$^{-1}$) characteristics of unsaturated oligomers described by the formula (I) or (II). $^1$H-NMR spectrum of the oligomer component composition exhibits characteristic signals: two overlapping doublets at δ 1.3 ppm (for methyl groups of the ether units [—CH—(CH$_3$)—O—CH(CH$_3$)—] and two overlapping quadruplets at δ 4.2 ppm (for methyne group of this ether unit).

4.4 A method for obtaining these compositions comprises heating the diols (D) with carboxylic acids (CA), preferably with methacrylic acid (MAA) (at mole ratio D:CA (MAA) 1:0.5–2.5, in the presence of a sulfocationites, such as Amberlite IPR-69 or Amberlyst XN-1010 ion-exchange resin, strongly acidic, macroreticular, high surface-area suitable for non-aqueous applications in aromatic solvent at the boiling temperature of the reaction mixture, with removing the reaction water evolving during the resin's synthesis.

The second class of the novel resins also represents related divinylaromatic compositions with a wide and various ratio of monomers and oligomers of different molecular weight (i.e., with different molecular weight distribution) comprising:

5–99% by weight of:
aryl compounds comprising at least one non-alkylated or alkylated aryl group and two vinyl groups attached directly to aromatic rings, such as diaryl compounds comprising at least two aryl groups linked together directly as in biphenyl or bridged by a linking group, each of said at least two aryl groups having a vinyl group attached thereto, such as
p-(CH$_2$=CH—Ar)$_2$O, p-(CH$_2$=CH—Ar)$_2$S, p-(CH$_2$=CH—Ar)$_2$, p,p'-CH$_2$=CH—Ar—Ar—CH=CH$_2$, bis-(4-vinylphenyl) ether (or its counterparts or related compounds where the ether linkage is replaced with sulfur, methylene (or methine) group or it is absent where vinylaryl group is directly linked together, and 1–75% by weight of:
unsaturated dimer of said divinylaromatic monomer, such as p—CH$_2$=CH—Ar—CH(CH$_3$)—CH=CH—Ar—CH=CH$_2$, 0.1–40% by weight of:
unsaturated trimer of said divinylaromatic monomer, such as

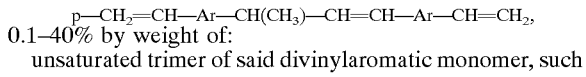

wherein n=1, 0.1–30% by weight of:
unsaturated tetramer and oligomer homologs of said divinylaromatic monomer, such as

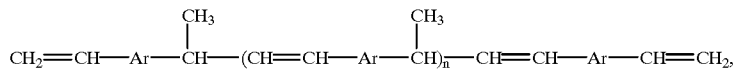

wherein n=2–30.

Proceeding from the practical applications, novel divinylaromatic compositions may be subdivided into two types comprising different less wide compositions with less wide range of components:

1. Divinylaromatic compositions riched with divinylaromatic monomer comprising at least the following components [examples 32–39]:

75–99% by weight of:
aryl compounds comprising at least one non-alkylated or alkylated aryl group and two vinyl groups attached directly to aromatic ring, such as diaryl compounds comprising at least two aryl groups linked together directly as in biphenyl or bridged by a linking group, each of said at least two aryl groups having a vinyl group attached thereto, such as

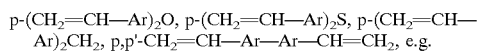

bis-(4-vinylphenyl) ether (or its counterparts or related compounds where the ether linkage is replaced with sulfur, methylene (or methine) group or it is absent where vinylaryl group is directly linked together, and 0.2–24% by weight of:
unsaturated dimer of said divinylaromatic monomer, such as p—CH$_2$=CH—Ar—CH(CH$_3$)—CH=CH—Ar—CH=CH$_2$, and
0.1–10% by weight of:

unsaturated trimer of said divinylaromatic monomer, such as

wherein n=1, and
0.1–1% by weight of:
unsaturated tetramer and higher oligomer homologs of said divinylaromatic monomer, such as

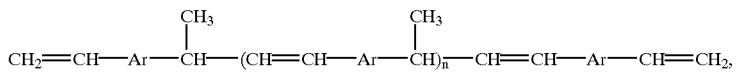

wherein n=2–4,
Unsaturated divinylaromatic compositions rich with divinylaromatic monomer and a novel method for obtaining the pure divinylaromatic monomer, such as

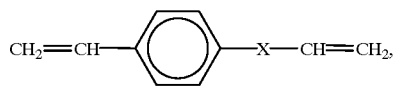

wherein X=aryl, alkylated aryl, biaryl, tri-aryl, O-aryl, O-alkylated aryl, S-aryl, S-alkylated aryl, $CH_2$-aryl, $CH_2$-alkylated aryl, etc., with high yield are of great interest for a lot of applications.

1.1 A method for obtaining these compositions comprises heating the diols in the presence of relatively the lowest concentration of a sulfonic acid, such as p-toluenesulfonic acid (TSA) (monohydrate) (mainly 0.5–10.0 mmole/L), preferably 1.0–3.0 mmole/L) in aromatic solvent, preferably in o-xylene, at the boiling temperature of the reaction mixture in the range of 100–160° C., preferably at ~144–150° C., finishing the dehydration process after removing the reaction water.

1.1.1 A method of obtaining pure divinylaromatic monomer by treatment of the composition described above and obtained according to the separation and purification of the monomer by recrystallization or sublimation of the monomer from the composition by its heating at, for example, 80 to 150° C. under vacuum.

It can be seen that these compositions have a number of the important distinctions (concerning qualitative and quantitative composition of resin, i.e., content, structure, properties, and molecular weight of divinylaromatic monomer, its dimer, and other components) from the previous unsaturated compositions (prototype) considered in the section "Background of the Art". In comparison with the previous resins, the resins (compositions) of the invention have the higher level of unsaturation. In contrast to divinylbenzene which is a tech., 55%, mixture of isomers (see, e.g., Aldrich, catalogue number 16,909-9) comprising also 3- and 4-ethylvinylbenzene, ethylbenzene and diethylbenzene, divinylaromatics proposed in this invention can comprise practically pure materials (95–99.5% of purity), provide a lower toxicity divinyl aromatic monomer (as compared to the divinyl benzene) and have only the intended amount (usually small (1–5%) amount) of its dimer and trimer. It should be emphasized that the dimer and trimer are identical or similar (related) compounds with respect to their properties. They should not be substantially considered as impurities. As to their functionality and reactivity, they are not practically different from the divinylaromatic monomer except with respect to the degree of crosslinking, and can be effectively used with the divinyl monomer (i.e., a composition) as crosslinking agents.

The novel method for obtaining the inventive compositions and, in fact, divinylaromatic monomers with the high or even quantitative yields also have significant distinctions. Enriching the unsaturated compositions with divinylaromatic monomer (up to 95–99% of theor.) and, consequently, decreasing in amount and molecular weight of oligomer homologs is attained under the following conditions established only now:

1. Using di-sec. aromatic diols, such as BHEPE only after a special (alkali) purification procedure for avoiding phenolic adducts in the claimable compositions,
2. Performance of the synthesis of the product in slightly polar aromatic solvents, such as toluene or, preferably, o-xylene at the boiling temperatures in the range of 100 to 160° C., preferably at 110–150° C., more preferably at 130–145° C.
3. Performance of the synthesis at the lowest concentration of acidic catalyst, such as TSA or sulfuric acid, preferably in the range of 0.5 to 6 mmole/L, preferably 1 to 3 mmole/L.
4. Performance of the synthesis at the lowest concentration (in the range of 0.05 to 0.3% of the weight of the diol) of the inhibitor of radical polymerization, such as hydroquinone or 4-tert-butyl catechol, for avoiding the deterioration of the composition by the above-mentioned impurities.

The previous method for obtaining divinylaromatic compositions was considerably different from the new one in missing the diol quality, the choice of aromatic solvent determining corresponding (boiling) temperature for the synthesis of the intended composition, etc.

2. Divinylaromatic compositions with increased molecular weight (increased viscosity), i.e., rich with oligomers of higher molecular weight comprising [examples 45–47]:
5–75% by weight of:
aryl compounds comprising at least one non-alkylated or alkylated aryl group and two vinyl groups attached directly to aromatic ring, such as diaryl compounds comprising at least two aryl groups linked together directly as in biphenyl or bridged by a linking group, each of said at least two aryl groups having a vinyl group attached thereto, such as

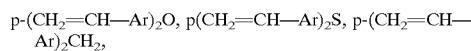

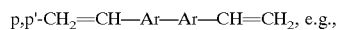

bis-(4-vinylphenyl) ether (or its counterparts or related compounds where the ether linkage is replaced with sulfur, methylene (or methine) group or it is absent where vinylaryl group is directly linked together, 20–75% by weight of:

unsaturated dimer of said divinylaromatic monomer, such as

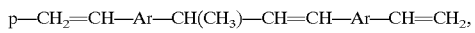
p—CH$_2$=CH—Ar—CH(CH$_3$)—CH=CH—Ar—CH=CH$_2$,

1–40% by weight of:

unsaturated timer of said divinylaromatic monomer, such as

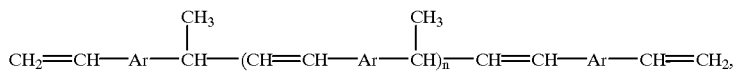

wherein n=1, and 0.5–30% by weight of:

unsaturated tetramer and higher oligomer homologs of said divinylaromatic monomer, such as

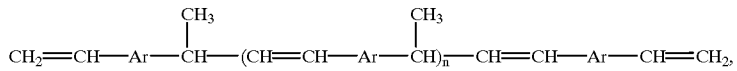

wherein n=2–30.

2.1 A method for obtaining these compositions comprises in heating the diols in the presence of relatively the highest concentration of sulfonic acid, preferably TSA (mainly 5–15 mmole/L) in aromatic solvent, preferably benzene, or toluene or o-xylene, at their boiling temperature with removing the reaction water evolving during the condensation process of the resin's formation. In the event of performing the resin's synthesis in toluene, o-xylene or other highly boiling aromatic solvents, after removing released water, the reaction mixture should be kept at 70–80° C. for a fixed period of time with or without adding of the extra amount of acidic catalyst depending on the intended characteristics of the resin.

The novel highly reactive resins of the invention are different from Rolivsan resins not only by quantitative and qualitative composition concerning the main components, but also by absence of adducts of phenolic impurities with monomers (M1 and M2), and unsaturated oligomers, such as:

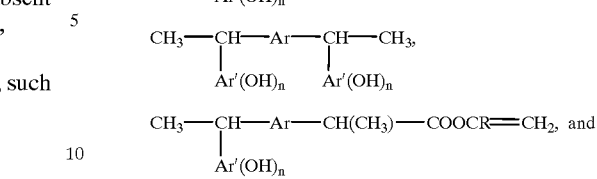

-continued

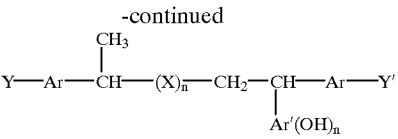

The novel resins of the invention may also differ and may also be differentiated from the Rolivsan resins described in the USSR Inventor's certificates by each of the following descriptions:

The compositions of the present invention comprise at least three monomers and oligomers comprising at least one diaryl compound comprising at least two aryl groups linked together directly or bridged by a linking group, each of said at least two aryl groups having a vinyl group attached thereto, at least one a methacrylic acid ester of a vinyl-substituted sec-ethylol-diaryl oxide or its thioether or methine counterpart, and at least one dimethacrylic acid esters of bis-[4(1-hydroxyethyl)aryl] ether, thioether or methine, and highly unsaturated oligomers having mainly formulae (I) and/or (II): (I)

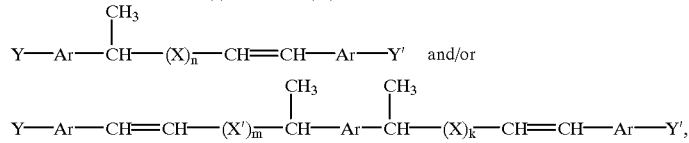

wherein Ar=Ph—Ph, Ph—O—Ph, Ph—13 Ph, Ph—CH$_2$—Ph, etc., X=CH(CH$_3$)—Ar—CH=CH, X'=CH=CH—Ar—CH(CH$_3$), Y=Y'=CH$_2$=CH—, CH$_2$=CR—COO—CH(CH$_3$)—, or Y=CH$_2$=CH—, Y'=CH$_2$=CR—COO—CH(CH$_3$)—, R=H, CH$_3$, alkyl (especially of C1 to C4), n=0–3, m=k=0, or m=1 and k=0, or m=0 and k=1, or m=k=1, defined by any one of: the fact that it may be photoinitiated (e.g., at least 20 or at least 30 number %, or at least 40%, or at least 50% or at least 75% reacted) at room temperature by $E_o=3\times10^{-3}$ W/cm$^2$ (e.g., from 1.0 to 10.0$\times10^{-3}$ W/cm$^2$, preferably from 1–5$\times10^{-3}$ W/cm$^2$) of UV radiation of 280–400 nm wavelength in 2 to 5 minutes in the presence of 0.5 to 1.5% by weight of different conventional photoinitiators, such as triarylsulfonium hexafluoroantimonate, triarylsulfonium hexafluorophosphate salts (cationic photoinitators) or benzil/benzoin ethers, acetophenone, and benzophenone types (free radical photoinitiators: Darocur and Irgacur, Merck), the fact that it is curable at temperatures of 60–80° C. or lower (e.g., at least 20 or at least 30 number %, or at least 40%, or at least 50% or at least 75% reacted) in the presence of an effective amount of conventional thermal curing (free radical) catalyst or initiator, such as benzoyl peroxide.

Novel resins are photosensitive and gelated by the UV radiation of weak intensity (exposition ($H_0$) is 0.4 to 0.9 W/cm$^2$ or (0.4–0.9)$\times10^7$ erg/cm$^2$). For comparison, Rolivsan resins are not photosensitive and cannot be gelated and cured by much more powerful UV radiation ($E_0$=~12$\times$10$^3$ W/cm$^2$) of 280–400 nm wavelength even for one or two weeks (i.e., >(6–12)$\times10^5$s or for $H_0$=(7.2–14.4)$\times10^{10}$ erg/cm$^2$ or 7.2–14.4 kJ/cm$^2$) and in the presence of the highest concentration (>5 wt-%) of a free radical photoinitiator, such as Darocur.

Rolivsan resins also cannot be gelated and cured at temperatures 20–120° C. thermally and/or in the presence of 1–5 wt-% and higher a thermal initiator, such as benzoyl or acetyl peroxide, tert-butyl hydroperoxide, methyl ethyl ketone peroxide, and/or dicumyl peroxide, etc. even over extensive periods of time;

and/or has less than 1% by weight of impurity selected from the group consisting essentially of monoaryl hydroxy compounds, especially monoaryl monohydroxy compounds, and monoaryl dihydroxy compounds where only one hydroxy group is attached directly to the aryl ring;

and the presence of comonomers selected from the group consisting of different unsaturated (vinyl and/or acetylene), epoxy, and other polyfunctional monomeric and oligomeric compounds, such as styrene, substituted styrenes (e.g., styrene sulfonate as is used in the manufacture of liquid chromatographic media of crosslinked polystyrenesulfonate) methylmethacrylate, acrylonitrile, maleic anhydride and other unsaturated anhydrided, acrylamide, (bis)maleimides, (meth)acrylic acid, vinylester resins, unsaturated polyester and epoxy resins, glycidyl methacrylate, phenol-formaldehyde resins, phenylacetylene, low molecular weight carboxyl, amine, or hydroxyl-terminated butadiene-acrylonitrile rubbers (reactive liquid rubbers etc.), (meth)acrylate-terminated polyurethanes. The published Inventors Certificates described above show the polymerization of the old, impure resins with only maleic anhydride (and other unsaturated anhydrides), (bis) maleimides, unsaturated polyesters, unsaturated epoxy resins, phenol-formaldehyde resins, and reactive liquid rubbers. Importantly, those copolymers were only available with high temperature (140–258 degrees Centigrade) cure.

Some of these compounds, such as maleic anhydride and other unsaturated anhydrides, unsaturated polyester, phenol-formaldehyde and epoxy resins had been applied also for modifications of Rolivsan resins with using only high temperature schedules (140–250° C. for curing the systems (B. A. Zaitsev and Kiseleva R. F. USSR Inventor's Certificate No. 910,694, Appl. 2,804,987/23-05, Jun. 19, 1979, Cl. C 08 L 63/00, B 32 B 27/30, B 32 B 27/38, UDC 678.686.(088.8).

Compound; Russian Patent No. 1,381,957, Appl. 4,026,359/23-05, Feb. 25, 1986, Cl. C 08 L 67/06, UDC 678.674 (088.8), Authors of Invention: B. A. Zaitsev, R. F. Kiseleva, and I. S. Andreeva, Patentee: Boris A. Zaitsev. Composition for obtaining cured polyester resins). In contrast to the previous (Rolivsan) resins, the novel resins of the invention may be easily copolymerized with them at the much lower temperatures (20–80° C. and higher).

Besides, the following new composites and compositions may be prepared and cured on the basis of the novel resins with: different reinforcements, fillers, and porous materials, e.g., fiberglass or fiberglass cloth, carbon or graphite fibers or fiber cloth, polyamide and polyimide fibers or fiber cloth, boron fibers, fine divided alumina, silica, aluminum plates with porous alumina layer (examples 7–11, 14, 26, 47–49).

The novel resins can be used directly for electric insulation with high temperature index (250–320° C.), automotive industry, (micro)electronics, etc. for: liquid processing, long-term solid prepreg technology, dry lay-up, potting, embedding, encapsulating, molding, laminating, vacuum pressure impregnation.

A List of Field of Use of Novel (Zaitform) Resins

1. Electrical insulation polymer compounds with lower viscosity at 20° C. and elevated [e.g., up to 315° C. (600° F.)] working temperature (with the use of the drop-by-drop-impregnating-drying process for one component (package solventless compositions) for bonding (after cure) the winding of the electric motors/generators (for working in the medium of mineral oil (IPM-10), in air, at high level of humidity). Temperature range:—60 to +315° C., working time: 200° C./500 hours, or 315°/80 hours (in oil), 203° C./5000 hours (in air), 250° C./880 hours, 315° C./82 hours (in air). Resource is five years.

Other applications: sealing compounds for electronics and electro-technics (transformers, windings, condensers).

The objective: The creation of the impregnating polymer compounds having:

(a) High electrical and mechanical properties both in the initial state (after curing) and after the exposure of high temperature (up to about 315° C. or 600° F.).

(b) Resistant to the treatment of the synthetic oils using at working temperatures (200° C. and over).

(c) Low viscosity providing the use of the drop-impregnating method.

(d) Low shrinkage.

(e) High corrosion resistance.

(f) Low toxicity.

(g) Low emission of volatile products at curing.

(h) Absence of solvents.

(i) Long shelf-time and convenient gelation time.

(k) One-stage crosslinking without volatile by-products evolution.

(l) Absence of bubbles and pores at and after curing.

TABLE 1

Some Thermal and Physical Properties of the Novel Resins

| | Values |
|---|---|
| Linear Coefficient of Thermal Expansion, $10^{-6}$, $K^{-1}$ for | |
| 30 to 100° C. | 40 |
| 100 to 200° C. | 50 |
| 200 to 300° C. | 55 |
| 300 to 320° C. | 80 |

TABLE 1-continued

Some Thermal and Physical Properties of the Novel Resins

| | Values |
|---|---|
| Thermal Conductivity Coefficient, W/mK, for: | |
| 25° C. | 0.25 |
| 175° C. | 0.50 |
| 250° C. | 0.55 |
| 300° C. | 0.60 |
| Specific Heat Capacity, J/kg K, for: | |
| 25° C. | 1000 |
| 175° C. | 1200 |
| 250° C. | 2000 |
| 300° C. | 2200 |
| Moisture pick up at relative humidity 95% at 40 ± 2° C. for 48 hours | 1.5 |

TABLE 2

Effect of Temperature on the Electrical Properties of Zaitform Resins

| Temperature, ° C. | $\rho_v$, Ohm · m | $\rho_v$, Ohm · m | tan δ[a)] ($10^3$ Hz) | ε[b)] ($10^3$ Hz) | E, MV/m (kV/mm) |
|---|---|---|---|---|---|
| −60 | — | — | $5.5 \times 10^{-3}$ | 2.9 | — |
| RT | $3 \times 10^{14}$ | $1 \times 10^{14}$ | $4.9 \times 10^{-3}$ | 2.9 | 36 |
| 180 | $4 \times 10^{12}$ | $1 \times 10^{12}$ | $3.3 \times 10^{-3}$ | 3.1 | — |
| 200 | $3 \times 10^{11}$ | $1 \times 10^{11}$ | $4.4 \times 10^{-3}$ | 3.1 | 32 |
| 250 | $5 \times 10^{8}$ | $5 \times 10^{8}$ | $3.1 \times 10^{-3}$ | 3.1 | 32 |
| 300 | $1 \times 10^{8}$ | $7 \times 10^{7}$ | $5.8 \times 10^{-3}$ | 3.7 | 32 (275° C.) |

[a)] Dielectrical losses
[b)] Dielectric constant

TABLE 3

Effect of Humidity on the Electrical Properties of Zaitform Resins

| Properties | RT | After exposure at 40 ± 2° C. and 95 ± 2% of relative humidity for 2 days | After exposure at 40 ± C. and 95 ± 2% of relative humidity for 28 days |
|---|---|---|---|
| tan δ (at $10^3$ Hz) | $(4.9 \pm 0.7) \times 10^{-3}$ | $(6.6 \pm 0.3) \times 10^{-3}$ | $(6.7 \times 0.3) \times 10^{-3}$ |
| tan δ (at $10^6$ Hz) | $(1.1 \pm 0.1) \times 10^{-2}$ | $(1.9 \pm 0.2) \times 10^{-2}$ | $(1.9 \pm 0.2) \times 10^{-2}$ |
| ε ($10^3$ Hz) | 2.9 ± 0.1 | 3.2 ± 0.6 | 3.2 ± 0.6 |
| ε ($10^6$ Hz) | 2.7 ± .1 | 3.0 ± 0.2 | 3.1 ± 0.3 |
| $\rho_v$, Ohm · m | $1 \times 10^{14}$ | $1 \times 10^{14}$ | $3 \times 10^{13}$ |
| E[*)], MV/m | 36 ± 0 | 32 ± 2 | 30 ± 3 |

[*)] Dielectric strength, MV/m

TABLE 4

Effect of High-Temperature Aging in Air on the Electrical Properties of Zaitform Resins

| Aging T, ° C. | Exposure time, hrs | $\rho_v$, Ohm · m | Dielectric strength, MV/m |
|---|---|---|---|
| 200 | 0 | $1 \times 10^{14}$ | 32 ± 2 |
| 200 | 500 | $1 \times 10^{14}$ | 35 ± 2 |
| 200 | 6000 | $3 \times 10^{13}$ | 40 ± 2 |
| 250 | 0 | $1 \times 10^{14}$ | 32 ± 2 |
| 250 | 800 | $2 \times 10^{14}$ | 41 ± 2 |
| 275 | 0 | $1 \times 10^{14}$ | 32 ± 2 |
| 275 | 350 | $4 \times 10^{13}$ | 42 ± 3 |
| 275 | 500 | $2 \times 10^{11}$ | 42 ± 4 |
| 315 | 30 | $1 \times 10^{14}$ | — |
| 315 | 40 | $8 \times 10^{13}$ | — |
| 315 | 60 | $1 \times 10^{13}$ | — |
| 315 | 80 | $4 \times 10^{13}$ | — |

TABLE 5

Some Properties of the Cured Zaitform Resin Used for Dielectric Primers[*)]

| Properties | at 20° C. | at 300° C. |
|---|---|---|
| Specific surfacial electrical resistance, $\rho_s$, Ohm | $12 \times 10^{12}$ | $5.7 \times 10^{12}$ |
| Specific volume electrical resistance, $\rho_v$, Ohm · m | $12 \times 10^{14}$ | $3.5 \times 10^{10}$ |
| Electrical strength | 36 | 23 |
| Dielectrical constant | 3 | — |
| tan δ $10^3$ Hz | $5 \times 10^{-3}$ | — |
| tan δ at $10^6$ Hz | $1 \times 10^{-2}$ | — |

[*)] Before priming, aluminum plate was heated at 420° C.

According to conventional processing for the printed microcircuit board, metallic layers of Cr—Cu—Cr were spray-coated on the surface of anodic aluminum with the following results:

1. Adhesion of the Zaitform resin to $Al_2O_3$-layer was high (150 kg/cm$^2$).
2. Adhesion of the spray-coated layers of Cr was 100–120 kg/cm$^2$.
3. The cured Rolivsan resin resisted the Cr-etching medium (HCl solution at 60–80° C.).
4. Coating prepared from the Zaitform resin provides protection from the electrical breakdown and the leakage currents.
5. Impregnating/priming microcracks of the oxide ($Al_2O_3$) layer.
6. Attaining the very low priming surface roughness of primed aluminum plates (as for highest class polishing).
7. Zaitform's coating resistance (no cracking) to dipping solder bath (at 300° C.): without decrease in adhesion, the cured Rolivsan resins to the oxide ($Al_2O_3$)-surfacial layer and without deterioration of dielectric properties.

TABLE 6

Adhesion of the Spray-Coated Layer of an Alloy (Russian Trade Name PC-3710-Alloy No. 30 [96% Cr + 4% Al]) Containing Cu to the Primed (by the Cured Zaitform Resin) the Aluminum Plate with the Oxide ($Al_2O_3$)-Surfacial Layer.

| Specimens No. | 1 | 2 | 3 | 4 | 5 | 6 | 7 |
|---|---|---|---|---|---|---|---|
| Pick-off force[a], kg | 2.9 | 2.6 | 2.4 | 4.0 | 4.0 | 2.8 | 2.6 |
| Adhesion, kgf/cm² | 170 | 153 | 141 | 235 | 235 | 165 | 153 |

[1]For the spary-coated film, the pick-off force was measured by means of the metal rod (with diameter of 1.5 mm) soldered to the spray-coated layer (printed circuit board).

Film's pick-off character was adhesionic, i.e., along interface between the spray-coated film/layer and the primed aluminum plate.

Vibration resistance test

Testing with resonant machine (frequency range 5 to 2,000 Hz, amplitude 5 g, time 27 hours and impact test (impact resistance) showed the coated material to be vibration-proof.

Number of impact acts was 1,000 with acceleration 10 g and frequency 60 impact acts/minute. After the above testing, specific surfacial electrical resistance of the primed (by Zaitform resin) aluminum plates, $\rho_s$, was over $5 \times 10^{10}$ Ohm. Electrical tension for testing was over 300 V. The thickness of the dielectrical layer was ~25 micrometers.

TABLE 7

Electrical Properties of the Primed Aluminum Plates After Specimens' Testing in the Tropical Chamber (Humidity Was Maintained 95% at 40° C. for 144 Hours (6 Days)

| Properties | Values |
|---|---|
| $\rho_s$ (at 100 V), Ohm | $4 \times 10^{10} - 2 \times 10^{11}$ |
| Tension for insulating layer's breakdown, V | 460–650 |

Conclusion: Aluminum substrates with combined electrical insulation obtained from a porous $Al_2O_3$ layer impregnated with Zaitform resins (the primed aluminum plates) have successful withstood the tropical testing.

The requirements to resistance and reliability for electrical engines of a new generation (temperature range 300–400° C.) are provided with impregnating and sealing polymer compounds having heat distortion temperature (range 150–250° C.) and thermal stability (not less than 400° C.) and high level of moisture resistance.

High temperature (working temperature range –60 to 300–320° C.) and erosion-resistant primer (protective coating) for paddles, blades made from the combination of alloy of boron-aluminum and carbon fiber composite with porous surface vacuum-impregnated with Zaitform resin MV-1 filled with the fine silical flour for engines of a new generation. The thickness of the coating was 0.08–0.2 mm; resource of work was 2,000 hours (100 hours at maximal temperature).

TABLE 8

Clear Castings and Glass Fiber Cloth Laminate Based on Zaitform Resin for Withstanding to the Gaseous hydrogen fluoride (HF) Medium at the Temperature of 100–120° C. and Under High Pressures (500–600 mm Hg)

| Cure at T, ° C. | Shape, size, mm | The Initial weight, g | Exposure time, hours | HF pressure, mm Hg | Amount of HF in the specimen, mg/g | Final weight, g | Appearance |
|---|---|---|---|---|---|---|---|
| 300 | Plate, 20 × 25 × 4 | 4.3 | 24 | 600 | 5 | 4.1 | Practically without changing |

Development of long-term preimpregnation compounds for aircraft and aerospace industries (examples 48, 49)

Development of the specific low melting formulations and the cure methods aimed at long-term non-tacky prepregs and advanced high-temperature easy-processable composites preparation.

The low-melting formulations of two different types have been developed for reinforcements impregnation:

1. The formulation A [example 40], i.e., unsaturated polyester modified with novel divinylaromatic composition of the invention (for composites with the working temperature range of 121–204° C. [250–400° F.]) is a new patentable low-melting formulation (binder A) (with temperature range of melting 60 to 70° C. and gelatin time 10 (@140° C.) to 40 minutes (@125° C.) which comprises, e.g., ordinary styreneless and solventless unsaturated polyester resin or vinylester resin (as chief ingredient), such as NPS 609-21M (Russian trade name for the formulation comprising the solution of polyethyleneglycolemaleatephthalate in dimethacrylate of triethyleneglycol), commercially available modifiers, thermoinitiators, antioxidant, flow control agent, and the novel divinylaromatic composition (high temperature crosslinking agent).

2. Formulation B [example 41] (for composites with the working temperature range of 232–316° C. [450–600° F.]) is a new patentable low-melting formulation with temperature range of melting 80 to 90° C. and gelation time 50 minutes (@140° C. comprising: Zaitform vinylester resins, novel divinylaromatic composition, and commercially available modifiers, thermoinitiators, antioxidant, and flow control agent.

TABLE 9

Adhesion Strength of Zaitform and Epoxy (EDT-10) Resin as Binder for Polyarylimide Fibers

| Binder | Non-effective fiber length, mm | Diameter of mono-fiber, mm | Average strength of mono-fiber, Mpa | Strength of adhesion interaction, Mpa |
|---|---|---|---|---|
| Zaitform | 1.78 | 0.0191 | 1730 ± 68 | 26 ± 0.8 |
| Epoxy | 1.67 | 0.0191 | 1730 ± 68 | 26.4 ± 1.1 |

TABLE 10

Some Properties of Carbon Fiber (Elur-P-01)[a)] Composites

| Matrices | Viscosity, cPs (T) | Fibers | $T_g$, °C. | $V_f$[b)], % | $\sigma_f$[c)], MPa | $\sigma_f/F_f$, MPa | $k_r$[d)] |
|---|---|---|---|---|---|---|---|
| Zaitform | 500 (RT) | Carbon | 310 | 60 | 1310 | 2183 | 87 |
| PEI-DPO | ~1 × 10$^4$ (320° C.) | Carbon | 240 | 44 | 780 | 1773 | 74 |
| IPM | ~1 × 10$^4$ (320° C.) | Carbon | 250 | 47 | 1030 | 2191 | 91 |
| Epoxy | 700 (RT) | Carbon | 160 | 55 | 1251 | 2275 | 91 |

[a)]For fiber Elur-P-01, tension strength was 2400–2700 Mpa.
[b)]Volume % of filling.
[c)]Flexural strength at RT.
[d)]Coefficient of the level of the fiber strength's realization.

TABLE 11

Some Properties of Polymer Fiber (Elur-P-01) Composites

| Binder | Fiber | $T_g$, °C. | Tension strength[a)], Mpa | Tension strength[b)], Mpa | $V_f$, % |
|---|---|---|---|---|---|
| Zaitform | Kevlar | 260–280 | 3700–3800 | 2100–2200 | 65 |
| Epoxy | Kevlar | 85–90 | 4400–4500 | 2500–2600 | 55 |
| Rolivsan | Polyarylimid | 260–280 | 1800–1900 | — | 65 |
| Epoxy | Polyarylimid | 85–90 | 2100–2200 | — | 55 |

[a)]For microplastic specimen,
[b)]For winding specimen

TABLE 12

Water Resistance of Fiberglass Cloth Laminate Based on the Cured Zaitform Resins

| Final cure T ° C. | Water pick up, % 1 day | 10 days | 30 days | Flexural after 0 h | Strength boiling 2 h | Mpa 30 days at RT |
|---|---|---|---|---|---|---|
| 180 | 1.19 | 2.45 | 2.58 | 210 | 191 | 184 |
| 250 | 0.72 | 1.4 | 1.53 | 290 | 290 | 350 |
| 275 | 0.37 | 1.42 | 1.72 | — | 310 | 323 |
| 300 | 0.33 | 1.36 | 1.6 | — | — | 300 |

TABLE 13

Dielectrical Properties of Fiberglass Cloth Laminate Based on the Cured Zaitform Resins Under Tropical Testing in the Chamber ($\phi = 98\%$, T = 40° C.)

| Sample No. | ε 0 | Tan δ 0 | ε 1 day | Tan δ 1 day |
|---|---|---|---|---|
| 1 | 3.55 | 0.0058 | 3.54 | 0.0086 |
| 2 | 3.47 | 0.0050 | 3.53 | 0.0085 |

TABLE 14

Dependence of Dielectrical Properties of the Fiberglass Cloth Laminate Based on the Cured Zaitform Resins on Temperature and Time of Aging

| Characteristics at 10$^6$ Hz | Aging 100 h | at 200 h | 250° C. 300 h | 500 h | Aging 100 h | at 300° C. 200 h |
|---|---|---|---|---|---|---|
| ε | 3.8 | 3.8 | 3.9 | 3.8 | 3.7 | 3.2 |
| Tan δ | 0.0079 | 0.0083 | 0.0080 | 0.0084 | 0.0050 | 0.0032 |
| $\rho_v$, Ohm · m | 1.15 × 10$^{15}$ | 8.7 × 10$^{14}$ | 4.33 × 10$^{13}$ | 1.15 × 10$^{15}$ | 1.0 × 10$^{15}$ | 6.19 × 10$^{14}$ |
| $\rho_s$, Ohm | 8.1 × 10$^{15}$ | 10$^{14}$ | 4.18 × 10$^{13}$ | 10$^{14}$ | 6.9 × 10$^{14}$ | 10$^{14}$ |

The novel resins of the invention may also differ and may also be differentiated from the Rolivsan resins described in the USSR Inventor's certificates by each of the following descriptions:

The compositions of the present invention comprise at least three monomers and oligomers comprising at least one diaryl compound comprising at least two aryl groups linked directly or bridged by a linking group, each of said at least two aryl groups having a vinyl group attached thereto, at least one a methacrylic acid ester of a vinyl-substituted sec-ethylol-diaryl oxide or its thioether or methine counterpart, and at least one dimethacrylic acid ester of bis-[4-(1-hydroxyethyl)aryl] ether, thioether or methine, which composition may be photoinitated at room temperature.

Novel resin compositions also comprise the three monomer systems of ingredients and oligomers comprising at least one diaryl compounds comprising at least two aryl groups linked directly or bridged by a linking group, each of said at least two aryl groups having a vinyl group attached thereto, at least one a methacrylic acid ester of a vinyl-substituted sec-ethylol-diaryl oxide or its thioether or methine counterpart, at least one dimethacrylic acid ester of bis-[4-(1-hydroxyethyl)aryl] ether, thioether or methine and highly unsaturated oligomers defined by any one of: and/or has less than 1% by weight of impurity selected from the group consisting essentially of monoaryl hydroxy compounds, especially monoaryl monohydroxy compounds, and monoaryl dihydroxy compounds where only one hydroxy group is attached directly to the aryl ring; and the presence of comonomers selected from the group consisting of ethylenically unsaturated, free-radical polymerizable comonomers, as are well known in the art.

Beads of styrene-divinylbenzene resins made by suspension polymerization are known to be used as the basis of ion-exchange resins. The largest use of DVB is in ion-exchange resins for domestic and industrial water softening. Ion-exchange resins are also used as solid acid catalysts for certain reactions, such as esterification.

In synthesis of polymer sorbents, such as styragel or shodex, structure and composition of the crosslinking agent are of great importance. It should be noted that common divinylbenzene comprises ~55% mixture comprising: 36.4% of meta-isomer and 18.6% of para-isomer, ~38% of ethylvinylbenzene, and small amount of diethylbenzene, (cf. the product made in Germany, Schuchardt Munchen). In principle, the crosslinks resulting from divinylbenzene should stabilize the bead structure and minimize swelling. In fact, the beads (grains) obtained with divinylbenzene exhibit low strength, especially, at swelling, and even failure (disintegration) and are not fit for regeneration.

The compositions and the pure divinylaromatic monomers of the invention provide much better control of network structure of the crosslinked polymers, the distribution of crosslinks and pores, improving solvent and chemical resistance of the sorbents, and their mechanical properties. The comparison of the calibration curves (FIG. 1) obtained for two columns of the same size, both with the styrene-divinylbenzene macroporous sorbent (KF-801) and the novel macroporous sorbent obtained according to example 51 shows that although both sorbents have the identic average pore size, they have distinct pore distributions and the components' resolution. More narrow pore distribution for a new sorbent provides increased selectivity of the components' separation (see FIG. 2 and example 51). Moreover, a new sorbent has the higher pore volume compared to the conventional sorbent (KF-801); it implies that a new sorbent has the enhanced separability.

FIG. 1. Calibration curves for two columns of the identic size with styrene-divinylbenzene macropores gel (KF-801) and a new (styrene-BVPE) macropores gel. The sorbents have identic average pore size, but they have different pore size distributions. Eluent is tetrahydrofuran, elution rate is 1 mL/minute, the size of columns is 0.8×30 cm, detector is refractometer.

FIG. 2. An example of separation of mixture of oligostyrene (with average molecular weight of 480 and benzene) with SEC on microcolumn (0.5×300 mm) with the gel of crosslinked copolymer of styrene with BVPE prepared according to example 51; eluent is methylethylketone, the flow rate is 3 microliter/minute, the inlet pressure was 34 atm.

The level of phenolic impurities in BHEPE and the related diols (the resins' precursors) may be easily controlled by observing the intensity of coloring phenolate ions. The full removal of phenolics by washing the precipitated diol will result in color disappearing wash water. Therefore, changing color of wash water in the BHEPE purification method of the invention may be considered as a very convenient purification control: the finished mother solution should be colorless. Thus, trace amount (<0.15%) of phenolics may be found by the color control. Using the color reaction of phenolics with the solution of ferric chloride is a more sensitive method for the phenolic impurities' control, i.e., for observation in the visible or UV region (Murray, M. J., Anal. Chem., 21:941 (1949); Smullin, C. F., Wetteran, F. P., Anal. Chem., 21:1836 (1955); Korenman, I. M. Fotometric Analysis. Methods of Determination of Organic Compounds. (In Russian), "Chemistry" Publ. Ch. 11, pp. 313, 317).

The description of the level of impurity should be clearly explained. As noted earlier, no previous purification method was ever used on the diol or resin which would have removed the phenolic monoaryl hydroxy substituted compounds. The minimum mol % of those phenolic impurities present in the resins was therefore at least about 1%, usually about at least 2 to 7 mol %. The recrystallization of the diol solution which had been performed in the old Rolivsan resins would have removed the non-phenolic mono-aryl hydroxy-substituted compounds, from their original concentrations equivalent to the concentrations of the phenolic mono-aryl compounds, but would not have removed the hydroxy phenolic monoaryl compounds.

The present invention also relates to novel polymer compositions, particularly novel crosslinked polymer compositions, and more particularly to polymers containing units derived from purified esters of diaryl compounds comprising at least two aryl groups linked directly together or bridged by a linking group, each of said at least two aryl groups having a vinyl group attached thereto, such as p-($CH_2$=CH—Ar)$_2$O, p-($CH_2$=CH—Ar)$_2$S, p-($CH_2$—CH—Ar)$_2$CH$_2$, p, p'-$CH_2$=CH—Ar—Ar—CH=CH$_2$, e.g., p,-($CH_2$=CH—$C_6H_4$)$_2$O, bis-(4-vinylphenyl)ether (or its counterparts where the ether linkage is replaced with sulfur or methine group or the rings are linked together directly), such as methacrylic ester of 4-vinyl-4'-(1-hydroxyethyl) diphenyloxide, or its counterparts where the ether linkage is replaced with sulfur or methine group or the rings are linked together directly as in biphenyl, and such as dimethacrylic ester of bis-[4-(1-hydroxyethylphenyl)] ether or its counterparts where the ether linkage is replaced with sulfur or methine group or the rings are linked together directly as in biphenyl, and such as unsaturated oligomers described by the above formulae (I), (II) or (III).

The previous Rolivsan Resin compositions variably contained at least 2% (on a mol basis of monoaryl hydroxy impurities), and usually at least 5% and up to at least 15% by mol basis (which is nearly equivalent to the weight basis) of the diol such as the BHEPE (bis-[4-(1-hydroxyethyl) phenyl] ether or 4,4'-bis-(sec-ethylol)diphenyloxide) used as an intermediate in the formation of products according to the teachings of the prior art was present as an unknown impurity.

A polymerizable composition, polymer, and method for preparation of a polymer is also described as part of this invention comprising forming a polymerizable composition comprising at least three monomers, said monomers and oligomers comprising:

2–95% by weight of:

diaryl compounds comprising at least two aryl groups linked together directly (as in biphenyl) or bridged by a linking group, each of said at least two aryl groups having a vinyl group attached thereto, such as p-(CH$_2$=CH—Ar)$_2$O, p-(CH$_2$=CH—Ar)$_2$S, p-(CH$_2$=CH—Ar)$_2$CH$_2$, p,p'-CH$_2$=CH—Ar—Ar—CH=CH$_2$, e.g., p-(CH$_2$=CH—C$_6$H$_4$)$_2$O, bis-(4-vinylphenyl)ether (or its counterparts where the ether linkage is replaced with sulfur or methine group or the rings are linked together directly), 2–65% by weight of:

a methacrylic acid ester of a vinyl-substituted sec-ethyloldiaryl oxide or its thioether or methine or biphenyl counterpart, e.g.,

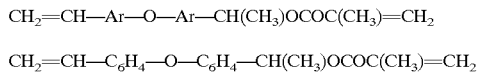

CH$_2$=CH—C$_6$H$_4$—O—C$_6$H$_4$—CH(CH$_3$)OCOC(CH$_3$)=CH$_2$ methacrylic acid ester of 4-vinyl-4'-(1-hydroxyethyl)-diphenyl-oxide or methacrylic ester of 4-vinyl-4'-(sec-ethylol)-diphenyloxide ether (or its counterparts where the ether linkage is replaced with sulfur or methine group or the rings are linked together directly), and 1–35% by weight of:

dimethacrylic acid esters of bis-[4-(1-hydroxyethyl)aryl] ether, thioether or methine or biphenyl counterpart, e.g.,

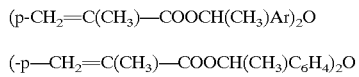

(-p—CH$_2$=C(CH$_3$)—COOCH(CH$_3$)C$_6$H$_4$)$_2$O dimethacrylic ester of bis-[4-(1-hydroxyethyl)phenyl] ether (or its counterparts where the ether linkage is replaced with sulfur or methine group or the rings are linked together directly) and, 2–95% by weight of:

unsaturated oligomers which can be described mainly by the formulae:

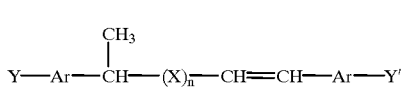

and/or

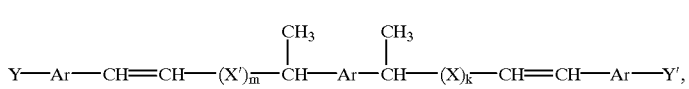

and

X=—CH(CH$_3$)—Ar—CH=CH—, X'=—CH=CH—Ar—CH(CH$_3$)—, Y=Y'=CH$_2$=CH—, CH$_2$=CR—COO—CH(CH$_3$)—, or Y=CH$_2$=CH—, Y'=CH$_2$=CR—COO—CH(CH$_3$)—, R=H, CH$_3$, alkyl (C$_1$ to C$_{15}$), n=0–3, m=k=0, or m=1 and k=0, or m=0 and k=1, wherein Ar is as defined above, and said reactive composition has less than 1% by weight of monoaryl phenolic compounds, and polymerizing said at least three monomers and oligomers to form a polymer. The reactive composition has less than 1%, preferably less than 0.8%, more preferably less than 0.7%, and still more preferably less than 0.5 or less than 0.2% by mol basis of the monoaryl phenolic impurities, such as described above.

The method and compositions may be practiced where the monoaryl phenolic impurities are present as less than 1% by weight of said at least three monomers and oligomers (preferably on a basis comparison to the first monomer only, the 2–95% by weight of diaryl compounds comprising at least two aryl groups bridged by a linking group, each of said at least two aryl A groups having a vinyl group attached thereto), less than 0.5% by weight, less than 0.25% by weight, down to 0% by weight of said at least three monomers and oligomers. The polymerizing may be performed at temperatures less than 100° C., less than 80 or 60° C., less than 40° C., less than 30° C., less than 25° C., and even at or less than 20° C. (e.g., room temperature or lower), and may be effected by low temperature free radical polymerization and photoinitiation, in large part because of the reduced amount of free radical inhibitor present.

The new resins of the present invention are referred to as Zaitform resins and the reactive compositions of the invention comprise blends of:

2–95% by weight of:

diaryl compounds comprising at least two aryl groups linked together directly (as in biphenyl) or bridged by a linking group, each of said at least two aryl groups having a vinyl group attached thereto, such as

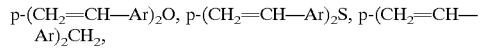

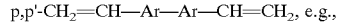

p-(CH$_2$=CH—C$_6$H$_4$)$_2$O, bis-(4-vinylphenyl) ether (or its counterparts where the ether linkage is replaced with sulfur or methine group or the rings are linked together directly), 2–65% by weight of:

a methacrylic acid ester of a vinyl-substituted sec-ethyloldiaryl oxide or its thioether or methine or biphenyl counterpart, e.g.,

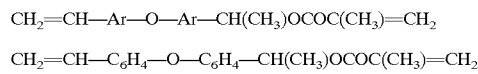

methacrylic acid ester of 4-vinyl-4'-(1-hydroxyethyl)-diphenyl-oxide or methacrylic ester of 4-vinyl-4'-(sec-ethylol)-diphenyloxide ether (or its counterparts where the ether linkage is replaced with sulfur or methine group or the rings are linked together directly), and 1–35% by weight of:

dimethacrylic acid esters of bis-alphahydroxyethyl(aryl) ether, thioether or methine, e.g.,

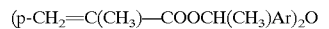

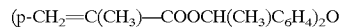

dimethacrylic ester of bis-[4-(1-hydroxyethyl)phenyl] ether (or its counterparts where the ether linkage is replaced with sulfur or methine group or the rings are linked together directly), and 2–95% by weight of:

unsaturated oligomers which can be described mainly by the formulae:

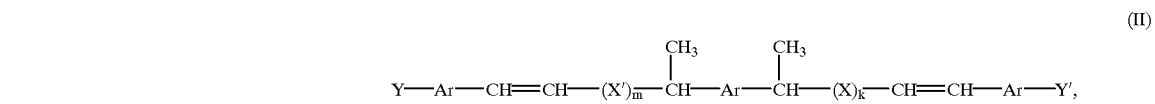

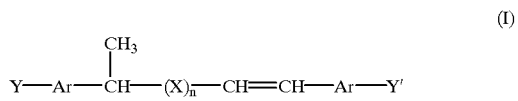

and/or

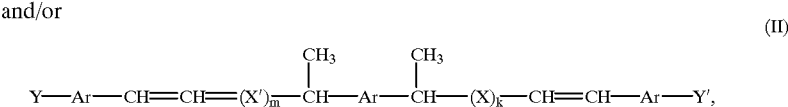

and

X=CH(CH$_3$)—Ar—CH=CH, X'=CH=CH—Ar—CH (CH$_3$), Y=Y'=CH$_2$=CH, CH$_2$=CR—COO—CH (CH$_3$), or Y=CH$_2$=CH, Y'=CH$_2$=CR—COO—CH (CH$_3$), R=H, CH$_3$, alkyl (C$_1$ to C$_{15}$), n=0–3, m=k=0, or m=1 and k=0, or m=0 and k=1, or m=k=1.

wherein Ar is as defined above, such as where

Monomer 1 is p-(CH$_2$=CH—C$_6$H$_4$)$_2$O, bis-(4-vinylphenyl)ether, wherein the phenyl group may or may not have additional substitution (e.g., for purposes of solubility, compatibility with other materials, oleophilic groups, oleophobic groups, hydrophilic groups, hydrophobic groups, ionic groups, etc.), Monomer 2 is

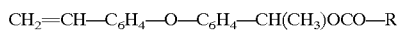

wherein R may comprise:

—C(CH$_3$)=CH$_2$, such as methacrylic ester of 4-vinyl-4'-(sec-ethylol-diphenyloxide, CHCH$_2$—, —C=CH, alkyl (e.g., of 1 to 20 carbon atoms), and the like, and Monomer 3 is

wherein R$^1$ is selected from C(CH$_3$)=CH$_2$, CH=CH$_2$, —C_—CH, alkyl, or the like, and unsaturated oligomers are the compounds described mainly by formulae (1), (II) or (III):

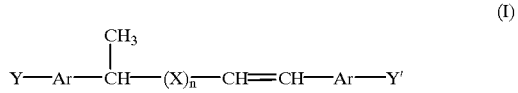

and/or and

X=CH(CH$_3$)—Ar—CH=CH, X'=CH=CH—Ar—CH (CH$_3$), Y=Y'=CH$_2$=CH, CH$_2$=CR—COO—CH (CH$_3$), or Y=CH$_2$=CH, Y'=CH$_2$=CR—COO—CH (CH$_3$), R=H, CH$_3$, alkyl (C$_1$ to C$_5$), n=0–3, m=k=0, or m=1 and k=0, or m=0 and k=1, or m=k=1.

COMPARATIVE EXAMPLES 1–6

Comparative Example of Prior and New BHEPE Synthesis

Example 1

(from previous practice) (B. A. Zaitsev, L. L. Dantsig, G. I. Khramova, and G. A. Shtraikhman, *J. App. Chem. of the USSR,* 50(2), 389–392 (1977):

A mixture of 20 g of skeletal Raney-nickel catalyst (particle size 0.08 and 0.5 mm, 250 mL ethyl alcohol and 76.2 g of BAPE were placed in an autoclave with a capacity of 0.5 liter and stirred at room temperature (19° C. to 40 or 50° C.) and with a hydrogen pressure of up to 100 atmospheres (40 to 100 atm.) until absorption of hydrogen ceased (0.5 h). The catalyst was then separated by centrifuging, the alcohol removed under reduced pressure, and the residue recrystallized from toluene (or benzene). The yield of the diol (BHEPE) was 55.5 g (71.5% of theoretical), mp 86–89° C. This process produced the heretofore unknown bye-products which will be discussed in greater detail later.

For the pilot scale production (manufacturing) of BHEPE, this method was modified to some extent and used in production of materials (but not published) as follows:

Example 2

From Previous Practice Unpublished Data

A mixture of 21.2 kg of suspension of skeletal Raney-nickel-titanium catalyst (consisting of 8.86 wt % of Ni, 0.57 wt % of Ti, and 90.57 wt % of ethyl alcohol, particle size about 0.25 mm), 37.4 kg of ethyl alcohol, and 14.92 kg of BAPE were placed in an autoclave with a capacity of 100 liters and stirred (at 150 revolutions/min) at heating up to 40–45° C. and with a hydrogen pressure of 2.0–2.5 MPa until absorption of hydrogen ceased (3–5 h). Then stirring was stopped for about 0.5 h for the catalyst's sedimentation, the reaction mixture was cooled to the room temperature, and the upper layer (the solution of the diol) was separated from the suspension of catalyst (the lower layer). After filtration of the upper layer, the alcohol was first distilled under normal pressure at 80–84° C., and at the end of the process (when the content of the alcohol decreased to 5–10%) under reduced pressure (10–15 mm Hg) and at 30–35° C. After the alcohol's removal, the raw BHEPE (14.0 kg) was dissolved in 13.27 kg of benzene at 70±5° C., and then, after hot filtration decreasing temperature of the benzene solution of raw BHEPE first to 30±5° C., then, to 2±2° C. for 3 hours and recrystallization, 12.4 kg (81.8% of theoretical) of BHEPE was obtained, mp 83–86° C.

These methods of synthesizing BHEPE, even after the purification practiced in production, were found by the present inventor to have not provided pure BHEPE products, and produced a product with adverse impurities which directly affected the properties of the final Rolivsan Resins. These impurities were not removed by any of the purification processes used on the BHEPE product. Certain of these impurity by-products (especially the phenolic compounds, described below) entered into an acid catalyzed alkylation reaction with unsaturated components of the resin and resulted in a product (polymeric resin) which had, in fact, markedly changed components, structure and composition (content, ratios) in comparison with the claimed results and contributed to a considerable deterioration of processing, product and other properties of the resins based on this BHEPE diol. Because a high level of a phenolic compound chemically attached to unsaturated components of a resin (which acts as an inhibitor of radical polymerization, e.g., possibly acting as free radical polymerization inhibitors or free radical scavengers), these resins could not be cured at low temperature, e.g., by photo(UV)-crosslinking, etc. The impurities also increased the viscosity of the resin, making it more difficult to coat. The impurities also caused brown coloration in the resin and the resulting polymer which reduced the range of utility for the resin where transparency or color purity was desired.

State Committee of Council of Ministers of the USSR on Invention and Discovery Description of invention in Inventor's Certificate No. 622258, Appl. 1,537,571/23–04, Jul. 15, 1971, Cl. C07C69/54, UDC 547.391.3, 562.4.07(088.8), Authors of Invention: R. G. Luchko, I. V. Sytova, B. A. Zaitsev, and G. A. Shtraikhman, Applicant: Institute of Macromolecular Compounds of the USSR Academy of Sciences was directed towards a Method of Obtaining Methacrylic Ester of 4-vinyl-4'-(sec-ethylol)-diphenyloxide. This invention of Inventor's Certificate No. 622258 (R. G. Luchko, I. V. Sytova, B. A. Zaitsev, and G. A. Shtraikhman, Inventor's Certificate No. 622258 (Appl. 1,537,571/23–04, Jul. 15, 1971, Cl. C07C69/54, UDC 547.391.3, 562.4.07 (088.8), Applicant: Institute of Macromolecular Compounds of the USSR Academy of Sciences. The method of obtaining methacrylic ester of 4-vinyl-4'-(sec-ethylol)-diphenyloxyde) is related to obtaining a new compound, the methacrylic ester of 4-vinyl-4'-(sec-ethylol)diphenyloxide which can be used as a binder for the preparation of glass fiber laminates and adhesives based on polymerizable oligomers. These materials yielded products with high temperature resistance and high thermal stability after curing of the oligomer. The well-known binders based on oligoglycolacrylates and oligoglycolmaleates obtained by esterifying glycols by unsaturated acids have not met the increasing requirements (concerning, first of all, heat resistance which does not reach 90 to 160° C. according to the Vicat softening point of plastics [ASTM D1525–85T]) for such materials. These tests are required by aircraft, aerospace industries, radioelectronics and other rapidly developing industries and engineering fields. The method of esterifying methacrylic acid by 4,4'-bis(sec-ethylol) diphenyloxide had been proposed, with an aim at obtaining a new polymerizable compound which could be used as a binder for the preparation of glass fiber laminates with high temperature resistance and high thermal stability. This process has been carried out in the presence of the acidic catalyst and an inhibitor of polymerization in the medium of organic solvent, such as benzene, at temperatures not higher than the boiling temperature of the reaction mixture.

Under those conditions of esterification, the glycol has undergone partial (incomplete) dehydration, yielding the monoester of methacrylic acid. As a result of the partial dehydration, the monoester obtained had vinyl end groups. The product obtained has provided a network (crosslinked) polymer with high thermal degradation resistant properties after its curing. Its heat resistance, as can be seen from thermomechanical curves recorded with the Institute of Physical Problems "IPhP" Vicat device, has reached 370–375° C., and thermal stability according to thermogravimetric analysis was 410° C. (for a maximum of 5% weight loss).

The Vicat softening point of plastics (American Specification ASTM D1525–85T: ASTM Standards on Plastics, Philadelphia, Pa., American Society for Testing Materials, 1959; Frazer A. N., High Temperature Resistant Polymers, Interscience Publ., N.Y., etc. 1968, p. 24) uses samples of a minimum width of ¾ in., and a thickness of ⅛ in. These samples are subjected to a load of 1000 g by a flat ended needle of 1 mm² cross-sectional area. The sample is heated in an immersion bath at a rate of 50° C./hr. The temperature is recorded when the indicator reads 1 mm penetration.

This type of device has been slightly modified by the IPhP (the Institute of Physical Problems) as a type of Vicat measuring device that could record needle penetration in the range from 0 to 1 mm.

Another class of the Rolivsan related unsaturated resins (Divinylaromatic Monomer-Oligomer Compositions) comprising one of the above-mentioned divinylaromatic monomers, bis (4-vinylphenyl) ether (BVPE), was also introduced by research done by Dr. Boris A. Zaitsev in 1979 (Russian Patent No. 802309, Appl. 2,746,230/23–05, Apr. 3, 1979, Cl. C08G63/64, C08L67/06, UDC 678.674 (088.8), Authors of Invention: B. A. Zaitsev and R. F. Kiseleva, Patentee: Boris A. Zaitzev]. This class of resins was referred to as monomer-oligomer compositions comprising
from about 1–57% by weight of:

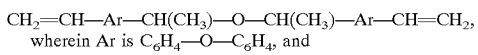
p-(CH$_2$=CH—C$_6$H$_4$)$_2$O, bis (4-vinylphenyl) ether (BVPE), and

2–25% by weight of unsaturated oligomers having the formula:

CH$_2$=CH—Ar—CH(CH$_3$)—O—CH(CH$_3$)—Ar—CH=CH$_2$,
wherein Ar is C$_6$H$_4$—O—C$_6$H$_4$, and 20–97 by weight of unsaturated oligomers having the formula:

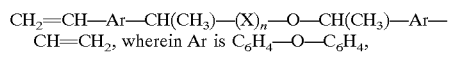
CH$_2$=CH—Ar—CH(CH$_3$)—(X)$_n$—O—CH(CH$_3$)—Ar—
CH=CH$_2$, wherein Ar is C$_6$H$_4$—O—C$_6$H$_4$, X is O—CH(CH$_3$)—Ar—CH(CH$_3$), n=1 to 5.

The objective of this class of resins was to increase the level of strength for heat stable polymer materials based on them and decrease their shrinkage during the preparation (processing).

The method for obtaining the resins was in heating bis-[4-(1-hydroxyethyl)phenyl] ether (BHEPE) in unpolar aromatic solvent at the temperature of boiling reaction mixture in the presence of a considerable amount of acidic catalyst, hydroquinone, cuprous chloride, and thiophene. According to the published method:

Example 3

(from previous practice) (Russian Patent No. 802309, Appl. 2,746,230/23–05, Apr. 3, 1979, Cl. C08G63/64, C08L67/06, UDC 678.674 (088.8), Authors of Invention: B. A. Zaitsev and R. F. Kiseleva, Patentee: Boris A. Zaitsev)

The mixture of 10.0 g of BHEPE, 0.1 g of hydroquinone (1% of BHEPE weight), 0.25 g of p-toluenesulfonic acid (TSA) (2.5% of BHEPE weight), 0.25 g of cuprous chloride, 0.05 g of thiophene, and 240 mL of benzene was heated at the boiling temperature for 10 minutes. After cooling, reaction mixture was separated from cuprous chloride by filtration, then it was washed subsequently with water, a 5% solution of sodium bicarbonate and water again to pH=7. The benzene solution was dried, passed through a layer of alumina, and benzene removed by distillation under vacuum in the presence of 0.01–0.1% hydroquinone. The yield of the composition was 7.5 g, $T_{softening}$ was 54–67° C., and its elemental analysis: Found, %: C 79.38, H 6.90, O 13.72. The composition's unsaturation, determined by the method of ozonolysis, was 0.0041 mol of double bonds per 1 g. An IR spectrum of the product exhibited the following characteristic absorption bands (cm$^{-1}$): 1625 (C=C), 1600, 1400, 1450 (C=C in aromatic ring), 1245 (—O— in aromatic ethers), 1100 [(CH(CH$_3$)—O—C(CH$_3$)], 990,910 (=CH$_2$ unplanar vibrations). According to the size-exclusion liquid chromatography (SEC) the composition had comprised: 1 wt-% bis (4-vinylphenyl) ether (BVPE), and 2 wt-% unsaturated oligomers having the formula:

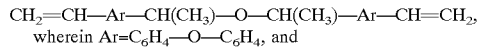

97 wt-% unsaturated oligomers having the formula:

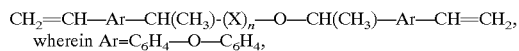

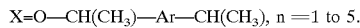

Example 4

(from previous practice) (Russian Patent No. 802309, Appl. 2,746,230/23–05, 3 Apr 1979, Cl. C08G63/64, C08L67/06, UDC 678.674 (088.8), Authors of Invention: B. A. Zaitsev and R. F. Kiseleva, Patentee: Boris A. Zaitsev)

The mixture of 10.0 g of BHEPE, 0.1 g (1% of BHEPE weight) of hydroquinone, 0.25 g (2.5% of BHEPE weight) of TSA, 0.25 g of cuprous chloride, 0.05 g of thiophene, and 240 mL of xylene was heated at the boiling temperature for 0.5 hr. The separation of the composition was carried out as described in the above Example 3. The yield of the composition was 8.2 g, T . was 55–65° C., and its elemental analysis: Found, %: C 85.45, H 6.93, 0 5.62. The composition's unsaturation was 0.00708 mol of double bonds per 1 g. According to SEC the composition had comprised: 49% wt-% bis (4-vinylphenyl) ether (BVPE), and 21 wt-% unsaturated oligomers having the formula:

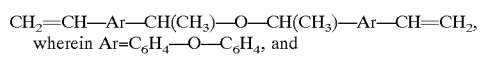

30 wt-% unsaturated oligomers having the formula:

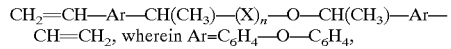

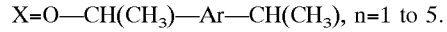

It should be noted that the method for obtaining Rolivsan resins had comprised very wide generalizations. As a result, the use of the proposed procedures led to formation of oligomeric components with uncontrolled amount, uncontrolled structure and uncontrolled molecular weight (and molecular weight distribution), and also with uncontrolled ratio of monomers and oligomers (uncontrolled compositions), a wide range of properties, and the polymerization reaction rates (R. G. Luchko, I. V. Sytova, B. A. Zaitsev, and G. A. Shtraikhman, Inventor's Certificate No. 622258 (Appl. 1,537,571/23–04, Jul. 15, 1971, Cl. C07C69/54, UDC 547.391.3, 562.4.07 (088.8), Applicant: Institute of Macromolecular Compounds of the USSR Academy of Sciences. Method of obtaining methacrylic ester of 4-vinyl-4'-(sec-ethylol)-diphenyloxyde).

Example 5

(from previous practice) (B. A. Zaitsev, L. L. Dantsig and L. G. Feoktistova. USSR Inventor's Certificate No. 927,835, Appi. 2,663,397/23–04, Sep 11, 1978, Cl. C08L 67/06, C08G 63/64, UDC 678.674 (088.8))

Obtaining unsaturated (oligomers) monomers at a molar ratio of BHEPE:acrylic acid=1:2.5.

The mixture of 10.0 g (0.0387 mol) of BHEPE, 0.1 g of hydroquinone (1% of BHEPE weight), 0.25 g of p-toluenesulfonic acid (2.5% of BHEPE weight), 0.25 g of cuprous chloride (CuCl), 100 mL of benzene, and 7.2 g (0.100 mol) of acrylic acid was heated at the boiling temperature of 75–85° C. for 1 hr 20 min. This resulted in 1.2 mL of reaction water. After cooling, the reaction mixture was separated by filtration from CuCl, then it was washed subsequently with water, and a 5% solution of sodium bicarbonate and water again. The benzene solution was dried over MgSO$_4$, passed through a layer (height 5 cm) of calcinated alumina, and the benzene distilled, obtaining ~9.4 g of the product, $n_D^{18}$ 1.595. Elemental analysis: Found, %: C 79.20, H 6.19, O 10.85. The ester number was 170.

Example 6

(from previous practice) (B. A. Zaitsev, L. L. Dantsig and L. G. Feoktistova. USSR Inventor's Certificate No. 927,835, Appl. 2,663,397/23–04, Sep 11, 1978, Cl. C08L 67/06, C08G 63/64, UDC 678.674 (088.8))

Obtaining monomer-oligomer composition at molar ratio BHEPE:acrylic acid =1:1. The mixture of 2.5 g (0.010 mol) of BHEPE, 0.05 g of hydroquinone (2.0% of BHEPE weight), 0.7 g of p-toluenesulfonic acid (28% of BHEPE weight), 0.07 g of cuprous chloride, 30 mL of benzene, and 0.72 g (0.010 mol) of acrylic acid was heated at the boiling temperature for 15 min. Then the reaction mixture was treated and the final product was separated as described in Example 1. The yield of the product was 1.5 g, $n_D^{31.5}$ 1.5844. Elemental analysis: Found, %: C 78.46, H 6.38, O 15.16. Iodine number (recalculated on the basis of bromine value determined on the result of brominating product according to Kaufman's method) was 104, and the ester number was 170.

Inventive Examples

A Corrected BHEPE Purification (ONE ASPECT OF THE PRESENT INVENTION)

Therefore, to complete the purification of BHEPE by removal of the phenolic impurities produced in Examples 1 and 2 above, the recrystallized product [obtained according to the method of Example 1 or Example 2 (100 g) was dissolved in 500 mL of 2% water-alcoholic [water:(ethyl) alcohol=~1:1 (by volume)] solution of NaOH at RT or 25–35° C. The solution becomes a dark-purple as a result of the presence of phenolics. Then the solution was poured out slowly by small portions with stirring into approximately six-fold amount of water. BHEPE precipitated as a white powder was isolated by filtration, washed repeatedly by water, then a 2% solution of HCl, water, and dried at 50–60° C. under vacuo. Changing color of wash water may be considered as a very convenient purification control: the finished mother solution should be colorless. Thus, trace amount (<0.15%) of phenolics may be found by the color control (Murray, M. J., *Anal. Chem.*, 21:941 (1949); Smullin, C. F., Wetteran, F. P., *Anal. Chem.*, 27:1836 (1955); Korenman, I. M. Fotometric Analysis. Methods of Determination of Organic Compounds. (In Russian), "Chemistry" Publ. Ch. 11, pp. 313, 317). The yield was 92 g, mp , ~91° C.

Quantitative Analysis of Phenolic Impurities in Bis-[4-((hydroxyethyl)phenyl] Ether (BHEPE) Produced on a Pilot Plant.

Photometric method of the determination of phenols was used and tailored for quantitative analysis of phenolic impurities in several batches of bis-[4-(1-hydroxyethly)phenyl] ether (BHEPE) produced on a pilot plant. The method was based on the formation of the color azo coupling of phenols with deazotized p-nitoraniline (Korenmen I. M. Photometric Analysis. Methods for the Determination of Organic Compounds. Moscow, Chemistry Publ., 1970, p. 43 (in Russian); Smith G., King D. Analyst 1964, 89, 305,312; 1965, 90, 55). The analysis was performed with photoelectrical colorimeter "PhEK-56M" for 35 minutes. As pattern for plotting the calibration curve was used sublimated p-cresol. Optical density of azo compounds was measured in the system of ethyl alcohol: water=1:4 at wavelength=490±10 nm in the cell of 50 mm. The accuracy of the analysis was 0.2%. The results of the analysis of the different samples of BHEPE are listed in Table.

TABLE

The results of the photometric analysis of phenolic impurities in bis-(1-hydroxethyl)phenyl] ether (BHEPE) produced on a pilot plant by the hydrogenation of bis-(4-acetylphenyl) ether with successive purification of the diol by recrystallization from benzene.

| Batch No. | Characteristics of the diol's batch | Content of phenolic impurities, wt. % |
|---|---|---|
| 1. | Industrial BHEPE (without additional purification), mp 82–84° C. | 1.32, 1.52, 1.43 |
| 2. | Industrial BHEPE (without additional purification), mp 83–85° C. | 0.34, 0.52, 0.87 |
| 3. | Industrial BHEPE (recrystallized from toluene), mp 86° C. | 0.18, 0.20 |
| 4. | Industrial BHEPE (recrystallized from aqueous ethyl alcohol), mp 86° C. | 0.20, 0.23 |
| 5. | Industrial BHEPE (after alkali water-alcohol purification), mp 89–91° C. | 0.10, 0.13 |
| 6. | Industrial BHEPE (after alkali water-alcohol purification), mp 89–91° C. | 0.09. 0.13 |
| 7. | Industrial BHEPE (after alkali wter-alcohol purification and recrystallization from toluene), mp 90–91° C. | 0.06, 0.07, 0.09 |

The present invention increases the yield of the target product and simplifies the process as compared to these alternative methods. Part of this benefit was realized due to divinylaromatic compositions riched with divinylaromatic monomer (75–99 wt-%) comprising at least the following components [examples 37–44]:

75–99% by weight of:
  aryl compounds comprising at least one non-alkylated or alkylated aryl group and two vinyl groups attached directly to aromatic ring, such as diaryl compounds comprising at least two aryl groups linked together directly as in biphenyl or bridged by a linking group, each of said at least two aryl groups having a vinyl group attached thereto, such as p-($CH_2$=CH—Ar)$_2$O, p-($CH_2$=CH—Ar)$_2$S, p-($CH_2$=CH—Ar)$_2$$CH_2$, p,p'-$CH_2$=CH—Ar—Ar—CH=$CH_2$, e.g., bis-4-vinylphenyl) ether (or its counterparts or related compounds where the ether linkage is replaced with sulfur, methylene (or methine) group or it is absent where vinylaryl group is directly linked together, and 0.2–24% by weight of:
  unsaturated dimer of said divinylaromatic monomer, such as

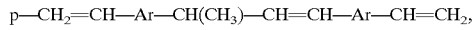

and 0.1–10% by weight of:
  unsaturated trimer of said divinylaromatic monomer, such as

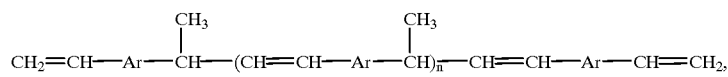

wherein n=1, and 0.1–1% by weight of:
  unsaturated tetramer and higher oligomer homologs of said divinylaromatic monomer, such as

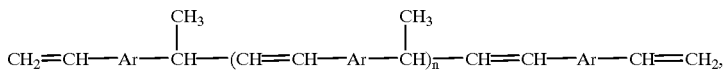

wherein n=2–4.

Unsaturated divinylaromatic compositions riched with divinylaromatic monomer (75–99 wt-%) and a novel method for obtaining the pure divinylaromatic monomer, such as

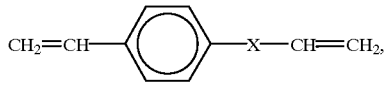

wherein X=aryl, alkylated aryl, biaryl, three-aryl, O-aryl, O-alkylated aryl, S-aryl, S-alkylated aryl, $CH_2$-aryl, $CH_2$-alkylated aryl, etc., with high yield are of great interest for a lot of applications.

A novel method for obtaining these compositions compromises heating the diols in the presence of relatively the lowest concentration of a sulfonic acid, such as p-toluenesulfonic acid (FSA) (monohydrate) (mainly 0.5–10.0 mmole/L), preferably 1.0–3.0 mmole/L) in aromatic solvent, preferably in o-xylene at the boiling temperature of the reaction mixture in the range of 100–160° C., preferably at ~144–150° C. with finishing the dehydration process after removing the reaction water. (examples, 37–44).

A novel method of obtaining pure divinylaromatic monomer is effected by treatment of the composition described herein and in 1.1 with separation and purification of the monomer by recrystallization or sublimation of the monomer from the composition by its heating at 80 to 150° C. under vacuum. The method proposed provides the increase in the yield up to 99% and a decrease in temperatures of the process.

The polymers, compositions and processes of the present invention have a wide range of utility in the coating art (for insulation, electrical resistance, solvent, chemical and corrosion resistance, thermal stabilization, binder application, and the like). The coating compositions may contain a wide range of conventional additives to improve specific objectives in the use of the polymers of the present invention. Such conventional additives include, but are not limited to such materials as dyes, pigments, UV absorbers, UV stabilizers, antistatic agents, lubricants, surfactants, fillers, coating aids, coupling agents (e.g., ambifinctional silanes and titanates), antioxidants, reducing agents, and the like. This invention is also related to obtaining unsaturated oligomers suited for the preparation of polymer materials—binders for making laminates, molding materials, potting, sealing and impregnating compounds, lacquers, coatings, and films.

Proposed compositions had considerable advantages over common oligomers and resins. They exceeded them for the set of the essential properties, including thermostability, strength of the products of their cure, and ease of their processing into polymer due to liquid viscous state of oligomer.

The polymers and glass-cloth laminates obtained on the basis on proposed methods have shown that the polymers obtained from the proposed compositions considerably exceeded for thermal stability and heat resistance the cured products obtained from conventional oligomers and resins having similar processing properties.

Examples for Zaitform (vinylester) resins rich with ester compounds, i.e., comprising M2+M3≧45 wt-% or ester number ≧120–140 (preferably 170–190) mg KOH/1 g of resin

Example 7

The mole ratio Diol (D): methacrylic acid (MAA)=1:3.05. The mixture of 40.00 g (0.1549 mole) of the purified bis-[4-(1-hydroxyethyl)phenyl] ether (BHEPE) 0.0803 g (0.20% of BHEPE weight) of 4-tert-butyl catechol, 0.1208 g (0.30% of BHEPE weight or 2.27 mmol/L) of TSA, 40.0 mL (40.6 g, or 0.4716 mole) of the freshly distilled methacrylic acid, and 200 mL of toluene was heated at the boiling temperature for 50 minutes. Water released during the dehydration was azeotroped from the system (5.5 ML). Then, the reaction mixture was washed successively by the distilled water, 2–3% solution of sodium bicarbonate ($NaHCO_3$), and by water again for attaining pH=7. The solution of the product in toluene was dried over $CaCl_2$, passed through a layer of alumina, and the solvent removed by distillation under the reduced pressure at 40° C. in the presence of about 0.040 g (0.1%) tert-butyl catechol. The yield was 36 g, $n_D^{21}$ 1.5680. The content of components according to Size Exclusion liquid Chromatography (SEC) was as follows, wt-%: Monomer M1, i.e., bis-(4-vinylphenyl) ether (BVPE) 9, Monomer 2 (methacrylic ester of 4-vinyl-4'-(1-hydroxyethyl)-diphenyloxide, or monoester) 38, Monomer 3 (dimethacrylic ester of bis-[4-(1-hydroxyethyl)phenyl] ether, or diester) 28, unsaturated oligomers (mixture of homologs) 25 which could be described by formula (I):

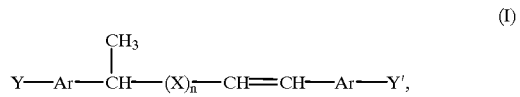

(I)

wherein Ar=Ph—O—Ph, X=CH($CH_3$)—Ar—CH=CH, Y=$CH_2$=CR—COO—CH($CH_3$), Y'=CH=$CH_2$, R=$CH_3$, n=0–3.

Gelation time of the resin (in the presence of 1 wt-% of Darocur (Merck photoinitiator for UV curing) was 3 minutes (the irradiation of luminescent lamp, 40 w, $E_e$=~3×10$^{-3}$ W/cm$^2$, $H_e$=0.54 Ws/cm$^2$ or 0.54×10$^7$ erg/cm$^2$).

For evaluation of this resin as a solventless thermally and heat stable matrix resin, fiberglass cloth laminates have been prepared with commercially available alkali-free alumoborosilicate fiberglass satin (8/3) weave cloth under Russian trade name "T-10-80" with the following characteristics: thickness 0.23 mm, weight 0.233 kg/m$^2$, diameter of elemental filament 6 microns, a number of fibers/cm 36+1 (warp), 20+1 (weft), breaking load (N) of fabric strip (25 mm×100 mm) is not less than 2700 (warp) and 1500 (weft). Five plies of the prepreg were stacked and heated in the temperature range 80–300° C. during several hours under the initial specific pressure about 1.0 kgf/cm$^2$. The laminates exhibited the following flexural strength values (after final cure temperature 300° C.), kgf, cm$^2$: 5170@20° C., 3370@250° C.

Example 8

The mole ratio Diol (D: methacrylic acid (MAA)=1:2.55. The mixture of 130.00 g (0.5033 mole) of the purified BHEPE 0.2400 g (0.185% of BHEPE weight) of 4-tert-butyl catechol, 1.300 g (1.0% of BHEPE weight or 5.34 mmol/L) of TSA, 108.7 mL (110.33 g, or 1.2816 mole) of the freshly distilled methacrylic acid, and 1040 mL of toluene was heated at the boiling temperature for 45 minutes. Water released during the dehydration was azeotroped from the system (17.0 mL). Then, reaction temperature was decreased to 70° C., it was kept at 70° C. for 1 hour, 10 minutes. After treatment as described above, the yield was 125 g, mp 48–50° C., $n_D^{55}$ 1.5785. The content of components according to SEC was as follows, wt-%: Monomer M1 (BVPE) 34, Monomer 2 (monoester) 37, Monomer 3 (diester) 10, unsaturated oligomers (mixture) which could be described by the formula (I) 19.

The samples of the fiberglass cloth laminates have been prepared as described above. Six plies of the prepreg were stacked and heated in the temperature range 80–250° C. during several hours under the initial specific pressure about 0.4 kgf/cm². The laminates exhibited the following flexural strength values (after final cure temperature 250° C.), kgf/cm²: 6400@20° C., 4100@250° C., and 1650@320° C.

The unidirectional carbon fiber composites have been prepared with Russian unidirectional carbon fiber tape. Nine plies of the prepreg were stacked and heated in the temperature range 80–300° C. during several hours under specific pressure about 10 kgf/cm². The composites had the following flexural strength values, kgf,/cm²: 12,000@20° C., 7600@250° C., 6200@320° C., 5200@350° C., 2400@400° C.

Example 9

The mole ratio Diol (D): methacrylic acid (MAA)=1:1.5. The mixture of 140.00 g (0.5420 mole) of the purified BHEPE 0.2800 g (0.20% of BHEPE weight) of 4-tert-butyl catechol, 0.2800 g (0.20% of BHEPE weight or 0.915 mmol/L) of TSA, 68.9 mL (69.93 g, or 0.8123 mole) of the freshly distilled methacrylic acid, and 1400 mL of toluene was heated at the * boiling temperature for 2 hours, 20 minutes. Water released during the dehydration was azeotroped from the system (16.0 mL). After treatment as described above, the yield was 146 g, mp 25–30° C., $n_D^{55}$ 1.5670. The content of components according to SEC was as follows, wt-%: Monomer M1 (BVPE) 17, Monomer 2 (monoester) 39, Monomer 3 (diester) 20, unsaturated oligomers (mixture) which could be described by the formula (I) 24.

For evaluation of this resin as a binder, the samples of the fiberglass cloth laminates have been prepared as described above. Five plies of the prepreg were stacked and heated in the temperature range 80–300° C. during several hours under the initial specific pressure about 1.0 kgf/cm². The laminates exhibited the following flexural strength values (after final cure temperature 300° C.), kgf/cm²: 5700@20° C., 3500@250° C., and 2900@250° C. (after aging in air at 320° C. for 10 hours).

Example 10

The mole ratio Diol (D): methacrylic acid (MAA)=1:2.56. The mixture of 100.00 g (0.3871 mole) of the purified BHEPE 0.200 g (0.20% of BHEPE weight) of 4-tert-butyl catechol, 1.000 g (1.0% of BHEPE weight or 5.34 mmol/L) of TSA, 84.0 mL (85.26 g, or 0.9904 mole) of three freshly distilled methacrylic acid, and 800 mL of toluene was heated at the boiling temperature for 40 minutes. Water released during the dehydration was azeotroped from the system (13.5 mL). Then, reaction temperature was decreased to 70° C.; it was kept at 70° C. for 1 hour, 10 minutes. After treatment as described above, the yield was 97.1 g, mp ~55° C., $n_D^{60}$ 1.5750. The content of components according to SEC was as follows, wt-%: Monomer M1 (BVPE) 36, Monomer 2 (monoester) 38, Monomer 3 (diester) 10, unsaturated oligomers (mixture) which could be described by the formula (I) 16.

Example 11

The mole ratio Diol (D): methacrylic acid (MAA)=1:1.5. The mixture of 100.00 g (0.3871 mole) of the purified BHEPE 0.200 g (0.20% of BHEPE weight) of 4-tert-butyl catechol, 0.2000 g (0.20% of BHEPE weight or 0.915 mmol/L) of TSA, 49.2 mL (49.94 g, or 0. 5801 mole) of the freshly distilled methacrylic acid, and 1000 mL of toluene was heated at the boiling temperature for I hour and 50 minutes. Water released during the dehydration was azeotroped from the system (12.2 mL). After treatment as described above, the yield was 105.8 g, $n_D^{40}$ 1.5680. The content of components according to SEC was as follows, wt-%: Monomer M1 (BVPE) 18, Monomer 2 (monoester) 42, Monomer 3 (diester) 23, unsaturated oligomers (mixture) which could be described by the formula (1) 17.

For evaluation of this resin as a binder, the samples of the fiberglass cloth laminates have been prepared as described above. Five plies of the prepreg were stacked and heated in the temperature range 80–300° C. during several hours under the initial specific pressure about 1.0 kgf/cm². The laminates exhibited the following flexural strength values (after final cure temperature 300° C.), kgf/cm²: 5200@20° C., 3000@250° C.

The unidirectional carbon fiber composites have been prepared with Russian unidirectional carbon fiber tape (commercially available under trade name "LUP-01": density 1.7 g/cm³, weight 35 g/m², number of fibers/10 cm 400 (warp), diameter of fiber 10–11 micron, porosity 3.5%, strength of 10 mm fiber 2.5 Gpa). Nine plies of the prepreg were stacked and heated in the temperature range 80–260° C. during several hours under specific pressure about 15 kgf/cm². The composites had the following flexural strength values, kgf/cm²: (after final cure temperature 260° C./1 hour): 12,000@20° C., 5700@250° C. and 5,000@320° C.; (after additional heating @320° C./2 hours): 4900@320° C., 4300@370° C., 1800@400° C.

Example 12

The mole ratio Diol (D): methacrylic acid (MAA)=1:2.5. The mixture of 10.00 g (0.0387 mole) of the purified BHEPE, 0.25 g (2.5% of BHEPE weight) of CuCl, 0.2497 g (2.5% of BHEPE weight or 13.30 mmol/L) of TSA, 8.2 mL (8.32 g, or 0.0967 mole) of the freshly distilled methacrylic acid, and 80 mL of toluene was heated at the boiling temperature for 25 minutes. After treatment as described above, the composition has the following characteristics: elemental analysis. Found, %: C 81.36, H 6.82; Unsaturation: 0.0070 mole of double bonds per 1 g. The content of components according to SEC was as follows, wt-%: Monomer M1 (BVPE) 44, Monomer 2 (monoester) 32, Monomer 3 (diester) 16, unsaturated oligomers (mixture) which could be described by the formula (I) 8.

Example 13

The mole ratio Diol (D): methacrylic acid (MAA)=1:1. The mixture of 10.00 g (0.0387 mole) of the purified BHEPE, 0.25 g (2.5% of BHEPE weight) of CuCl, 0.2503 g (2.5% of BHEPE weight or 14.01 mmol/L) of TSA, 3.30 mL (3.35 g, or 0.0389 mole) of the freshly distilled methacrylic acid, and 80 mL of benzene was heated at the boiling temperature for 1 and 2 hours after the first and second samplings were taken, respectively. After treatment as described above, elemental analysis: for the first sampling: Found, %: C 84.35, H 6.44; for the second sampling: Found, %: C 85.30, H 6.93. The composition's unsaturation determined by the method of ozonolysis was 0.0076 and 0.0066 mole of double bonds per 1 g for the first and second samplings, respectively. The content of components for the second sampling according to SEC was as follows, wt-%: Monomer M1 (BVPE) 35, Monomer 2 (monoester) 10, Monomer 3 (diester) 35, unsaturated oligomers (mixture) which could be described by the formula (I) 20.

Example 14

The mole ratio Diol (D): methacrylic acid (MAA)=1:1.52. the mixture of 120.00 g (0.4645 mole) of the purified BHEPE 0.2401 g (0.20% of BHEPE weight) of 4-tert-butyl catechol, 0.2400 g (0.20% of BHEPE weight or 0.914 mmol/L) of TSA, 60 mL (60.9 g, or 0.7074 mole) of the freshly distilled methacrylic acid, and 800 mL of toluene was heated at the boiling temperature for 1 hour, 20 minutes. Water released during the dehydration was azeotroped from the system. After treatment as described above, the yield was 124 g, $n_D^{40}$ 1.5665, $n_D^{20}$ 1.5750. The content of components according to SEC was as follows, wt-%: Monomer M1 (BVPE) 11, Monomer 2 (monoester) 31, Monomer 3 (diester) 23, unsaturated oligomers (mixture) which could be described by the formula (I) 35.

The resin's gelation time at 1400C was 18–20 minutes; gelation time (photo-crosslinking) at room temperature (19° C.) in the presence of 1 wt-% of Darocur (Merck photoinitiator for UV curing) was 1 minute, 40 seconds (the irradiation of luminescent lamp, 40 w).

For evaluation of this resin as a binder, the samples of the fiberglass cloth laminates have been prepared as described above. Five plies of the prepreg were stacked and heated in the temperature range 80–300° C. during several hours under the initial specific pressure about 1.0 kgf/cm². The laminates exhibited the following flexural strength values (after final cure temperature 300° C.), kgf/cm²: 0@20° C., 3800@250° C., and 3500@250° C. (after aging in air at 320° C. for 10 hours).

Example 15

The mole ratio Diol (D): methacrylic acid (MAA)=1:2.5. The mixture of 10.00 g (0.0387 mole) of the purified BHEPE, 0.0218 g (0.22% of BHEPE weight) of 4-tert-butyl catechol, 0.2501 g (2.5% of BHEPE weight or 13.35 mmol/L) of TSA, 8.2 mL (8.32 g, or 0.0967 mole) of the freshly distilled methacrylic acid, and 80 mL of toluene was heated at the boiling temperature for 0.5 (the first sampling). Then, reaction temperature was decreased to 75° C., it was kept at 75° C. for 3 hours (the second sampling) and 4 hours (the third sampling). After treatment as described above, the content of components according to SEC was as follows, wt-%. For first sampling: Monomer M1 40, Monomer 2 (monoester) 28, Monomer 3 (diester) 30, unsaturated oligomers (mixture) (which could be described by the formula (1) 2; for the second sampling: Monomer M1 15, Monomer 2 (monoester) 16, Monomer 3 (diester) 28, unsaturated oligomers (mixture) (which could be described by the formula (1) 41; for the third sampling: Monomer M1 11, Monomer 2 (monoester) 13, Monomer 3 (diester) 24, unsaturated oligomers (mixture) (which could be described by the formula (1) 52; $T_{soft}$ 43–50° C., $n_D^{40}$ 1.610.

Example 16

The mole ratio Diol (D): methacrylic acid (MAA)=1:2.5. The mixture of 10.00 g (0.0387 mole) of the purified BHEPE, 0.0203 g (0.20% of BHEPE weight) of 4-tert-butyl catechol, 0.2499 g (2.5% of BHEPE weight or 13.33 mmol/L) of TSA, 8.2 mL (8.32 g, or 0.0967 mole) of the freshly distilled methacrylic acid, and 80 mL of toluene was heated at the boiling temperature for 0.5 (the first sampling). Then, reaction temperature was decreased to 50° C., it was kept at 50° C. for 3.5 hours (the second sampling) and 5 hours (the third sampling). After treatment as described above, the content of components according to SEC was as follows, wt-%. For first sampling: Monomer M1 32, Monomer 2 (monoester) 22, Monomer 3 (diester) 30, unsaturated oligomers (mixture) (which could be described by the above formula) 16; for the second sampling: Monomer M1 18, Monomer 2 (monoester) 16, Monomer 3 (diester) 24, unsaturated oligomers (mixture) which could be described by the formula (I) 42; for the third sampling: Monomer M1 7, Monomer 2 (monoester) 8, Monomer 3 (diester) 10, unsaturated oligomers (mixture) which could be described by the formula (1) 75, $n_D^{40}$ 1.6040.

Example 17

The mole ratio Diol (D): methacrylic acid (MAA)=1:1.5. The mixture of 10.00 g (0.0387 mole) of the purified BHEPE, 0.010 g (0.1% of BHEPE weight) of 4-tert-butyl catechol, 0.2490 g (2.5% of BHEPE weight or 13.74 mmol/L) of TSA, 5.0 mL (5.075 g, or 0.0590 mole) of the freshly distilled methacrylic acid, and 80 mL of benzene was heated at the boiling temperature for 45 minutes (the first sampling), 2 hours (the second sampling), 3 hours (the third sampling), 3.5 hours (the fourth sampling). After treatment as described above, the content of components according to SEC was as follows, wt-%:

| Number of sampling (time) | M1 | M2 | M3 | Oligomers |
|---|---|---|---|---|
| 1 (45 minutes) | 15 | 32 | 30 | 23 |
| 2 (2 hours) | 11 | 12 | 30 | 47 |
| 3 (3 hours) | 9 | 12 | 20 | 59 |
| 4 (3.5 hours) | 4 | 4 | 10 | 82 |

Example 18

The mole ratio Diol (D): methacrylic acid (MAA)=1:1.42. Synthesis of the resin based on the diol with diphenyl methane unit was conducted in a four-neck, 250 mL round-bottom flask equipped with a mechanical stirrer, gas inlet, thermometer, Dean Stark trap, and condenser. The flask was charged with 10.0020 g (0.0413 mole) of the purified bis-[4-(1-hydroxyethyl)phenyl]-methane (BHEPM), 0.025 g (0.21%) of 4-tert-butyl catechol (inhibitor of free-radical polymerization), 100 mL of toluene (solvent and azeotroping agent), 4.96 mL (5.0334 g, or 0.5848 mole) of the freshly distilled methacrylic acid and, at stirring, 0.073 g (0.73% of the BHEPM weight or 3.34 mmole/L) of p-toluenesulfonic acid (monohydrate) (TSA) as acidic catalyst. This reaction mixture was, then, heated until the toluene began to reflux (at boiling point) about 102–11 1° C. for 2 hours, 30 minutes. An optimum reflux temperature range appears to be about 109–110 20 C. Water released during the dehydration was azeotroped from the system. Then, the reaction mixture was washed successively by the distilled water, 2–3% solution of sodium bicarbonate, and by water again for attaining pH=7.

The solution of the resin in toluene was dried over $CaCl_2$ passed through a layer of alumina, and toluene removed by distillation under vacuum in the presence of about 0.1% 4-tert-butyl catechol. The yield of the resin was 9.5 g, $n_D^{20}$ 1.5748. According to the reversed phase chromatography (column Separon Si C18, toluene was used as eluate, the elution rate was 0.1 mL/minute, a refractometric detector was used). The content of components was as follows, wt-%: Monomer M1 (BVPM) 25, Monomer 2 (methacrylic ester of 4-vinyl-4'-(1-hydroxyethyl)-diphenylmethane, or monoester) 58, Monomer 3 (dimethacrylic ester of bis-[4-(1-hydroxyethyl)phenyl]methane, or diester) 6, unsaturated oligomers (mixture) described by the formula (I) 11. They could be described by formula:

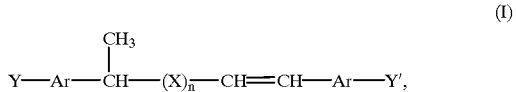

(I)

wherein $Ar=Ph-CH_2-Ph$, $X=CH(CH_3)-Ar-CH=CH$, $Y=CH_2=CR-COO-CH(CH_3)$, $Y'=CH=CH_2$, $R=CH_3$, $n=0-3$.

Example 19

The mole ratio Diol (D): methacrylic acid (MAA)=1:1.42. Synthesis of the resin based on the diol with diphenyl methane unit was conducted in a four-neck, 250 mL round-bottom flask equipped with a mechanical stirrer, gas inlet, thermometer, Dean Stark trap, and condenser. The flask was charged with 10.001 g (0.0413 mole) of the purified bis-[4-(1-hydroxyethyl)phenyl]-methane (BHEPM), 0.205 g (0.21%) of 4-tert-butyl catechol (inhibitor of free-radical polymerization), 100 mL of toluene (solvent and azeotroping agent), 4.96 mL (5.0344 g, or 0.05848 mole) of the freshly distilled methacrylic acid and, at stirring, 0.1602 (1.60% the BHEPM weight of 7.32 mmole/L) of TSA. This reaction mixture was, then, heated until the toluene began to reflux (at boiling point) about 102–111° C. for 3 hours, 45 minutes. An optimum reflux temperature range appears to be about 109–110° C. Water released during the dehydration was azeotroped from the system. The temperature has been decreased down to 70° C. for 1 hour. Then, the reaction mixture was cooled to room temperature, and treated as described above. The yield of the resin was 9.3 g, $n_D^{20}$ 1.5728. The content of components was as follows, wt-%: Monomer M1 (BVPM) 20, Monomer 2 (methacrylic ester of 4-vinyl-4'-(1-hydroxyethyl)-diphenylmethane, or monoester) 51, Monomer 3 (dimethacrylic ester of bis-[4-(1-hydroxyethyl)phenyl]methane, or diester) 17, unsaturated oligomers (mixture) described by the formula (I) 12.

Example 20

The mole ratio Diol (D): methacrylic acid (MAA)=1:1.42. The mixture of 10.00 g (0.03901 mole) of BHEPM 0.0204 g (0.2% of BHEPM weight) of 4-tert-butyl catechol, 0.3012 g (3.01% of BHEPM weight or 13.74 mmol/L) of TSA, 4.96 mL (5.0344 g, or 0.05848 mole) of the freshly distilled methacrylic acid, and 100 mL of toluene was heated at the boiling temperature for 2 hours, 40 minutes. Water released during the dehydration was azeotroped from the system. After treatment as described above, the yield of the resin was 9.1 g, $n_D^{20}$ 1.6010. The content of components was as follows, wt-%: Monomer M1 (BVPM) 7, Monomer 2 (methacrylic ester of 4-vinyl-4'-(1-hydroxyethyl)-diphenylmethane, or monoester) 62, Monomer 3 (dimethacrylic ester of bis-[4-(1-hydroxyethyl)phenyl] methane, or diester) 25, unsaturated oligomers (mixture) described by the formula (I) 6.

Example 21

The mole ratio Diol (D): methacrylic acid (MAA)=1:2.41. The mixture of 4.840 g (0.0200 mole) of the purified 4,4'-di-(1-hydroxyethyl)biphenyl (DHEBP) (mp 148–150° C.), 0.0145 g (0.3% of DHEBP weight) of 4-tert-butyl catechol, 0.3130 g (6.47% of DHEBP weight of 19.531 mmol/L) of TSA, 4.08 mL (4.14 g, or 0.0481 mole) of the freshly distilled methacrylic acid, and 75 mL of toluene was heated at the boiling temperature for: 40 minutes (the first sampling), 1 hour, 30 minutes (the second sampling), and 2 hours, 30 minutes (the third sampling). Water released during the dehydration was azeotroped from the system. Then, temperature was decreased to 70° C., and 0.1553 g of the extra amount of TSA was added to the residue (the fourth sampling). The reaction mixture was kept and stirred at 70° C. for 1 hour. After treatment of the samplings as described above, the content of components and other characteristics was given in the Table below:

| Number of sampling (time) | Yield g | Mp, ° C. | M1, wt-% | M2, wt-% | M3, wt-% | Oligomers described by the formula (I) |
|---|---|---|---|---|---|---|
| 1 (40 minutes) | 0.85 | 95–110 | 13 | 63 | 21 | 3 |
| 2 (1 hour, 30 minutes) | 0.95 | 110–115 | 12 | 54 | 12 | 22 |
| 3 (2 hours, 30 minutes) | 0.60 | 80–108 | 20 | 50 | 9 | 21 |
| 4 (3.5 hours) | 0.50 | 75–105 | 25 | 50 | 11 | 14 |

Example 22

The mole ratio Diol (D): methacrylic acid (MAA)=1:2.41. The mixture of 4.840 g =(0.0200 mole) of the purified 4,4'-di-(1-hydroxyethyl)biphenyl (DHEBP) (mp 148–150° C.), 0.0145 g (0.3% of DHEBP weight) of 4-tert-butyl catechol, 0.1550 g (3.2% of DHEBP weight or 9.71 mmol/L) of TSA, 4.08 mL (4.14 g, or 0.0481 mole) of the freshly distilled methacrylic acid, and 75 mL of toluene was heated at the boiling temperature for: 30 minutes (the first sampling), 2 hours (the second sampling). Water released during the dehydration was azeotroped from the system. Then, temperature was decreased to 70° C., and 0.0775 g of the extra amount of TSA was added to the residue (the third sampling). The reaction mixture was kept and stirred at 70° C. for 1 hour, 15 minutes. After treatment of the samplings as described above, the content of components and other characteristics was given in Table:

| Number of sampling (time) | Yield, g | M1, wt-% | M2, wt-% | M3, wt-% | Oligomers described by the formula (I) |
|---|---|---|---|---|---|
| 1 (30 minutes) | 0.95 | 34 | 28 | 13 | 25 |
| 2 (2 hours) | 0.90 | 71 | 15 | 3 | 11 |
| 3 (3 hours, 15 minutes) | 1.50 | 54 | 11 | 2 | 33 |

Example 23

The mixture of 10.00 g (0.03901 mole) of BHEPM 0.0205 g (0.20% of BHEPM weight) of 4-tert-butyl catechol, 0.3014 g (3.01% of BHEPM weight or 13.65 mmol/L) of TSA, 5.76 mL (5.846 g, or 0.0679 mole) of the freshly distilled methacrylic acid, and 100 mL of toluene was heated at the boiling temperature for 30 minutes for the first sampling. After that, the reaction mixture is refluxed for 1 hour. After treatment, the sampling and residue as described above, $n_D^{20}$ was 1.5750 and 1.5965 for the first sampling and the residue, respectively. The content of components was as follows, wt-%: for the first sampling, Monomer M1 (BVPM) 26, Monomer 2 (methacrylic ester of 4-vinyl-4'-(1-hydroxyethyl)-diphenylmethane, or monoester) 28, Monomer 3 (dimethacrylic ester of bis-[4-(1-hydroxyethyl)phenyl]methane, or diester) 11, unsaturated oligomers (mixture) 35 (formula III); for the second sampling, M1 55, M2 17, M3 2, unsaturated oligomers 26 (formula I).

Example 24

The mixture of 10.00 g (0.03901 mole) of BHEPM 0.0208 g (0.20% of BHEPM weight) of 4-tert-butyl catechol, 0.2508 g (2.51% of BHEPM weight or 11.36 mmol/L) of TSA, 5.76 mL (5.846 g, or 0.0679 mole) of the freshly distilled methacrylic acid, and 100 mL of toluene was heated at the boiling temperature for 45 minutes (the first sampling) with removing 1.1 mL the reaction water. Then, temperature was decreased to 70° C., and 0.3479 g of the extra amount of TSA was added to the residue (the second sampling). The reaction mixture was kept and stirred at 70° C. for 2 hours. The total yield is 8.711 g. After treatment of the samplings as described above, the content of components and other characteristics was given in Table:

| Number of sampling (time) | $n_D^{20}$ | M1, wt-% | M2, wt-% | M3, wt-% | Oligomers described by the formula (I) |
|---|---|---|---|---|---|
| 1 (45 minutes) | — | 24 | 31 | 13 | 32 |
| 2 (2 hours, 45 minutes) | 1.5823 | 24 | 21 | 4 | 51 |

Vinyl ester compositions with increased molecular weight (increased viscosity) and impoverished with ester endgroups, i.e., riched with oligomers of higher molecular weight.

Example 25

The mole ratio Diol (D): methacrylic acid (MAA)=1:0.1. The mixture of 10.0010 g (0.0387 mole) of the purified BHEPE 0.0110 g (0.11% of BHEPE weight) of 4-tert-butyl catechol, 0.0373 g (0.37% of BHEPE weight or 1.503 mmol/L) of TSA, 0.4 mL (0.406 g, or 0.00472 mole) of the freshly distilled methacrylic acid, and 120 mL of o-xylene was heated at the boiling temperature for 40 minutes. Water released during the dehydration was azeotroped from the system (~1.3 mL). After treatment as described above, the yield was 8.08, mp 85–87.5° C. The content of components according to SEC was as follows, wt-%: Monomer M1 (BVPE) 86, Monomer 2 (monoester) 2, Monomer 3 (diester) 1, unsaturated oligomers (mixture) which could be described by the formula (I) 11.

Example 26

The mole ratio Diol (D): methacrylic acid (MAA)=1:2.55. The mixture of 250.00 g (0.9678 mole) of the purified BHEPE 0.5016 g (0.20% of BHEPE weight) of 4-tert-butyl catechol, 6.2517 g (2.50% of BHEPE weight or 13.33 mmol/L) of TSA, 209 mL (212.14 g, or 2.4641 mole) of the freshly distilled methacrylic acid, and 2 L of toluene was heated at the boiling temperature for 1 hour. Water released during the dehydration was azeotroped from the system (35 mL). Then, reaction temperature was decreased to 70° C.; it was kept at 70° C. for 1 hour, 10 minutes. After treatment as described above, $n_D^{40}$ 1.5960. The content of components according to SEC was as follows, wt-%: Monomer M1 (BVPE) 23, Monomer 2 (monoester) 14, Monomer 3 (diester) ~2, unsaturated oligomers (mixture) which could be described by the formula (I) 61. The resin's gelation time at 140° C. was 14–18 minutes.

For evaluation of this resin as a binder, the samples of the fiberglass cloth laminates have been prepared as described above. Five plies of the prepreg were stacked and heated in the temperature range 80–300° C. during several hours under the initial specific pressure about 1.0 kgf/cm². The laminates exhibited the following flexural strength values (after final cure temperature 300° C.), kgf/cm²: 6000@20° C., 3600@250° C., and 3000@250° C. (after aging in air at 320° C. for 10 hours).

Example 27

The mole ratio Diol (D): methacrylic acid (MAA)=1:0.99. The mixture of 50.00 g (0.1936 mole) of the purified BHEPE, 0.050 g (0.1% of BHEPE weight) of 4-tert-butyl catechol, 1.2476 g (2.5% of BHEPE weight or 14.03 mmol/L) of TSA, 16.25 mL (16.49 g, or 0.1916 mole) of the freshly distilled methacrylic acid, and 400 mL of toluene was heated at the boiling temperature for 15 minutes with evolving 4.5 mL of the reaction water removed azeotropically. Then the temperature was decreased down to 80° C. for 0.5 hour and the reaction mixture was kept at 75–80° C. for 1 hour additionally. After treatment as described above (0.1 g of 4-tert-butyl catechol was added before toluene removing), the yield of resin was 41.0 g, $T_{softening}$ 60–75° C., $n_D^{80}$ 1.620, $n_D^{75}$ 1.622, $n_D^{60}$ 1.626. The content of components according to SEC was as follows, wt-%: Monomer M1 –60.

Example 28

The mole ratio Diol (D): methacrylic acid (MAA)=1:1.52. The mixture of 50.00 g (0.1936 mole) of the purified BHEPE, 0.048 g (0.1% of BHEPE weight) of 4-tert-butyl catechol, 1.2496 g (2.5% of BHEPE weight or 13.79 mmol/L) of TSA, 25.0 mL (25.375 g, or 0.2948 mole) of the freshly distilled methacrylic acid, and 400 mL of benzene was heated at the boiling temperature for 2.5 hours with evolving ~6.9 mL of the reaction water removed azeotropically. After treatment as described above, the content of components according to SEC was as follows, wt-%: Monomer M1 13, Monomer 2 (monoester) 12, Monomer 3 (diester) 30, unsaturated oligomers (mixture) (which could be described by the formula (1) 45, $n_D^{80}$ 1.605.

Example 29

The mole ratio Diol (D): methacrylic acid (MAA)=1:1.52. The mixture of 50.00 g (0.1936 mole) of the purified BHEPE, 0.0499 g (0.1% of BHEPE weight) of 4-tert-butyl catechol, 1.2492 g (2.5% of BHEPE weight of 13.79 mmol/L) of TSA, 25.0 mL (25.375 g, or 0.2948 mole) of the freshly distilled methacrylic acid, and 400 mL of benzene was heated at the boiling temperature for 2 hours. After treatment as described above, the content of components according to SEC was as follows, wt-%: Monomer M1 17, Monomer 2 (monoester) 13, Monomer 3 (diester) 29, unsaturated oligomers (mixture) which could be described by the formula (I) 41, $n_D^{20}$ 1.621.

Example 30

The mole ratio Diol (D): methacrylic acid (MAA)=1:2.55. The mixture of 130.00 g (0.5033 mole) of the purified BHEPE 0.2600 g (0.2% of BHEPE weight) of 4-tert-butyl catechol, 3.2500 g (2.5% of BHEPE weight of 13.33 mmol/L) of TSA, 108.7 mL (110.33 g, or 1.2816 mole) of the freshly distilled methacrylic acid, and 1040 mL of toluene was heated at the boiling temperature for 0.5 hour. Water released during the dehydration was azeotroped from the system (17.1 mL). Then, reaction temperature was decreased to 70° C., it was kept at 70° C. for 1 hour, 10 minutes. After treatment as described above, the yield was 111.4 g, mp <40° C., $n_D^{40}$ 1.6055. The content of components according to SEC was as follows, wt-%: Monomer M1 (BVPE) 28, Monomer 2 (monoester) 19, Monomer 3 (diester) 3, unsaturated oligomers (mixture) which could be described by formula (1) 50.

Example 31

The mole ratio Diol (D): methacrylic acid (MAA)=1:2.55. The mixture of 100.00 g (0.3871 mole) of the purified BHEPE 0.200 g (0.20% of BHEPE weight) of 4-tert-butyl catechol, 2.500 g (2.5% of BHEPE weight or 13.33 mmol/L) of TSA, 83.6 mL (84.85 g, or 0.9856 mole) of the freshly distilled methacrylic acid, and 800 mL of toluene was heated at the boiling temperature for 50 minutes. Water released during the dehydration was azeotroped from the system (12.5 mL). Then, reaction temperature was decreased to 70° C.; it was kept at 70° C. for 1 hour, 10 minutes. After treatment as described above, the yield was 81.4 g, mp 35–40° C., $n_D^{40}$ 1.6050. The content of components according to SEC was as follows, wt-%: Monomer M1 (BVPE) 26, Monomer 2 (monoester) 16, Monomer 3 (diester) 3, unsaturated oligomers (mixture) which could be described by the formula (I) 53.

Vinyl Ester Compositions with Middle Molecular Weight (Middle Viscosity Having Oligomers with Ether Units Obtained with Sulfocationites

Example 32

The mole ratio Diol (D): methacrylic acid (MAA)=1:2.50. The mixture of 10.00 g (0.0387 mole) of the purified BHEPE, 0.0203 g (0.20% of BHEPE weight) of 4-tert-butyl catechol, 8.2 mL (8.32 g, or 0.0967 mole) of the freshly distilled methacrylic acid, and 80 mL of toluene was heated with 2.50 g of an ion-exchange resin in H-form Russian trade name "KU-23", sulfonic acid functionality (strongly acidic), capacity ~2.1–2.5 meq/g similar to Amberlite IPR-69 ion-exchange resin, sulfonic acid functionality (strongly acidic), capacity 5 meq/g (dry) or Amberlyst XN-1010 ion-exchange resin, strongly acidic, macroreticular, high surface area suitable for non-aqueous applications (see, e.g., Aldrich Catalog) at the boiling temperature for 1 hour with releasing 1.0 mL of the reaction water (72% of theor.). Then, additional portion (3.0 g) of the "KU-23" resin was added to the reaction mixture and heating was prolonged for 13 hours. After treatment as described above, the content of components according to SEC was as follows, wt-%: Monomer M1 16, Monomer 2 (monoester) 16, Monomer 3 (diester) 28, unsaturated oligomers 40 which could be described by the formula (III).

Example 33

The mole ratio Diol (D): methacrylic acid (MAA)=1:2.50. The mixture of 10.00 g (0.0387 mole) of the purified BHEPE, 0.0203 g (0.10% of BHEPE weight) of 4-tert-butyl catechol, 5.0 mL (5.075 g, or 0.0590 mole) of the freshly distilled methacrylic acid, and 75 mL of toluene was heated with 3.0 g of an ion-exchange resin in H-form (Russian trade name "KU-23") at the boiling temperature for 14.5 hours with releasing 1.2 mL of the reaction water (86% of theor.). After treatment as described above, the content of components according to SEC was as follows, wt-%: Monomer M1 24, Monomer 2 (monoester) 14, Monomer 3 (diester) 30, unsaturated oligomers 32 which could be described by the formula (III).

Example 34

The mole ratio Diol (D): methacrylic acid (MAA)=1:1. The mixture of 10.00 g (0.0387 mole) of the purified BHEPE, 0.0106 g (0.10% of BHEPE weight) of 4-tert-butyl catechol, 3.25 mL (3.30 g, or 0.0383 mole) of the freshly distilled methacrylic acid, and 50 mL of toluene was heated with 3.0 g of the "KU-23" resin at the boiling temperature for 2 hours. Then, additional portion (1.0 g) of the "KU-23" resin was added to the reaction mixture and heating was prolonged for 10 hours. After treatment as described above, the content of components according to SEC was as follows, wt-%: Monomer M1 13, Monomer 2 (monoester) 22, Monomer 3 (diester) 28, unsaturated oligomers 37 which could be described by the formula (III).

Example 35

The mole ratio Diol (D): methacrylic acid (MAA)=1:0.5. The mixture of 10.00 g (0.0387 mole) of the purified BHEPE, 0.010 g (0.10% of BHEPE weight) of 4-tert-butyl catechol, 1.65 mL (1.675 g, or 0.0195 mole) of the freshly distilled methacrylic acid, and 30 mL of toluene was heated with 3.0 g of the "KU-23" resin at the boiling temperature for 5 hours. After treatment as described above, the content of components in the composition according to SEC was as follows, wt-%: Monomer M1 15, Monomer 2 (monoester) 15, Monomer 3 (diester) 27, unsaturated oligomers 43 which could be described by the formula (III), $n_D^{40}$ 1.597.

Example 36

The mole ratio Diol (D): methacrylic acid (MAA)=1:0.75. The mixture of 20.00 g (0.0774 mole) of the purified BHEPE, 0.0191 g (0.1% of BHEPE weight) of 4-tert-butyl catechol, 5.0 mL (5.075 g, or 0.0590 mole) of the freshly distilled methacrylic acid, and 60 mL of toluene was heated with 6.0 g of the "KU-23" resin at the boiling temperature for 5 hours. After treatment as described above, the content of components in the composition according to SEC was as follows, wt-%: Monomer M1 20, Monomer 2 (monoester) 24, Monomer 3 (diester) 32, unsaturated oligomers 24 which could be described by the formula (III).

Divinylaromatic Compositions Riched with Divinylaromatic Monomer

Example 37

The mixture of 120.00 g (0.4645 mole) of bis-[4-(1-hydroxyethyl)phenyl] ether (BHEPE), 0.12 g (0.1% of BHEPE weight) of 4-tert-butyl catechol, 0.3002 g (0.25% of BHEPE weight or 1.0114 mmol/L) of TSA, and 1.440 L of o-xylene was heated at the boiling temperature for 80 minutes. Water released during the dehydration was azeotroped from the system. Then, the reaction mixture was treated as described in Example 7. The yield of the unsaturated composition riched with bis-(4-vinylphenyl) ether (BVPE) was 100.5 g (97.3% of theor.), mp 85–87° C., gelation time for the composition stab with 0.3 wt-% of 4-tert-butyl catechol: 1–3 minutes at 120° C., 5–6 minutes at 100° C., 90 minutes at 90° C. According to size-exclusion liquid chromatography, the content of components was as follows, wt-%: Monomer M1 (BVPE) 95±3, its unsaturated dimer 5±3, its insaturated trimer and tetramers <0.5%. Recrystallized from ethyl alcohol, BVPE had purity of higher than 99.5% and mp 87–89° C.

Example 38

The mixture of 30.03 g (0.1163 mole or 0.2981 mole/L) of BHEPE, 0.030 g (0.1% of BHEPE weight) of 4-tert-butyl catechol, 0.1470 g (0.49% of BHEPE weight or 1.981 mmol/L) of TSA, and 360 mL of toluene was heated at the boiling temperature for 2 hours, 20 minutes. Water released during the dehydration was azeotroped from the system. Then, the reaction mixture was treated as described in Example 1. The yield of the unsaturated composition riched with bis-(4-vinylphenyl) ether (BVPE) was 25.0 g (96.7% of theor.), mp 84–86° C. According to size-exclusion liquid chromatography, the content of components was as follows, wt-%: Monomer M1 (BVPE) ~90, its unsaturated dimer ~9, its insaturated trimer and tetramers <1%. Recrystallized from ethyl alcohol, BVPE had purity of higher than 99.5% and mp 85–87° C.

Example 39

The mixture of 100.75 g (0.3900 mole or 0.9977 mole/L) of BHEPE, 0.108 g (0.1% of BHEPE weight) of 4-tert-butyl catechol, 0.1470 g (0.15% of BHEPE weight or 1.977 mmol/L) of TSA, and 290 mL of o-xylene was heated at the boiling temperature for 3 hours. Water released during the dehydration was azeotroped from the system. Then, the reaction mixture was treated as described in Example 1. The yield of the unsaturated composition rich with bis-(4-vinylphenyl) ether (BVPE) was 25.0 g (96.7% of theor.), mp 82–86° C. According to size-exclusion liquid chromatography, the content of components was as follows, wt-%: Monomer M1 (BVPE) ~80, its unsaturated dimer ~18, its insaturated trimer and tetramers <2%.

Example 40

The mixture of 10.02 g (0.0391 mole) of bis-[4-(1-hydroxyethyl)phenyl]-methane (BHEPM) 0.010 g of 4-tert-butyl catechol, 0.125 g (1.248% of BHEPM weight or 5.050 mmole/L) p-toluenesulfonic acid (monohydrate) (TSA), and 120 mL of o-xylene was heated at the boiling temperature for 1.5 hours. Water released during the dehydration was azeotroped from-the system. Then, the reaction mixture was washed successively by the distilled water, 2–3% solution of sodium bicarbonate (NaHCO$_3$), and by water again for attaining pH=7. The solution of the product in o-xylene was dried over CaCl$_2$ passed through a layer of alumina, and the solvent removed by distillation under the reduced (1–2 mm Hg) pressure at 40° C. in the presence of about 0.00168 g tert-butyl catechol. The yield of the unsaturated composition riched with bis-4-vinylphenyl) methane (BVPM) was 7.59 g (88% of theor.), mp 30–33° C., $n_D^{40}$ 1.603. According to the reversed phase chromatography (column Separon Si C 18, toluene was used as eluate, the elution rate was 0.1 mL/minute, a refractometric detector was used). The content of components was as follows, wt-%: Monomer M1 (BVPM) 79, its unsaturated dimer 16.5, its insaturated trimer 4, unsaturated tetramer and higher oligomers <0.5%. The pure BVPM (purity was >99.5%), mp 36–38° C. was obtained by sublimation of the monomer at 130° C. for 1 hour under vacuum (1–2 mmHg).

Example 41

The mixture of 10.00 g (0.03901 mole) of BHEPM, 0.0093 g (0.093% of BHEPM weight) of 4-tert-butyl catechol, 0.1022 g (1.022% of BHEPM weight or 4.13 mmole/L) of TSA, and 120 mL of o-xylene was heated at the boiling temperature for 2 hours. Water released during the dehydration was azeotroped from the system. Then, the reaction mixture was treated as described in Example 1. The yield of the unsaturated composition riched with BVPM was 7.9 g (91.9% of theor.), mp 31–34° C., $n_D^{40}$ 1.604. According to reversed phase chromatography, the content of components was as follows, wt-%: Monomer M1 (BVPM) 87, its unsaturated dimer 10.5, its insaturated trimer 2%, tetramer and higher oligomers <0.5%. The pure BVPM (purity was >99.5%), mp 36–38° C. was obtained by sublimation of the monomer at 130° C. for 1 hour under vacuum (0.5 mm Hg).

Example 42

The mixture of 5.0020 g (0.02064 mole) of 4,4'-di-(1-hydroxyethyl)biphenyl (DHEBP), 0.0050 g (0.1% of DHEBP weight) of 4-tert-butyl catechol, 00742 g (1.483% of DHEBP weight or 4.11 mmol/L) of TSA, and 90 mL of o-xylene was heated at the boiling temperature for 40 minutes. Water released during the dehydration was azeotroped from the system. Then, the reaction mixture was treated as described in Example 1. The yield of the unsaturated composition riched with 4,4 '-divinylbiphenyl (DVBP) was 3.8 g (89.3% of theor.). According to reversed phase chromatography, the content of components was as follows, wt-%: Monomer M1 (DVBP) 77, its unsaturated dimer 17, its insaturated trimer 5%, tetramers and higher oligomers <1%. The pure DVBP (purity was >99.5%), mp 150–153° C. was obtained by sublimation of the monomer at 160° C. for 1 hour under vacuum (1–2 mm Hg).

Example 43

The mixture of 5.00 g (0.0206 mole) of 4,4'-di-(1-hydroxyethyl)biphenyl (DHEBP), 0.0050 g (0.1% of DHEBP weight) of 4-tert-butyl catechol, 00542 g (1.08% of DHEBP weight or 3.00 mmol/L) of TSA, and 90 mL of o-xylene was heated at the boiling temperature for 1 hour. Water released during the dehydration was azeotroped from the system. Then, the reaction mixture was treated as described in Example 1. The yield of the unsaturated composition riched with 4,4 '-divinylbiphenyl (DVBP) was 4.10 g (96.5% of theor.). According to reversed phase chromatography, the content of components was as follows, wt-%: Monomer M1 (DVBP) 89, its unsaturated dimer 8.5, its insaturated trimer 2%, tetramers and higher oligomers <0.5%. The pure DVBP (purity was >99.5%), mp 150–153° C. was obtained by sublimation of the monomer at 160° C. for 1 hour under vacuum (1–2 mm Hg).

Example 44

The mixture of 4.99 g (0.0206 mole) of 4,4'-di-(1-hydroxyethyl)biphenyl (DHEBP), 0.0047 g (0.1% of DHEBP weight) of 4-tert-butyl catechol, 00903 g (1.81% of DHEBP weight or 5.00 mmol/L) of TSA, and 90 mL of toluene was heated at the boiling temperature for 2 hours. Water released during the dehydration was azeotroped from the system. Then, the reaction mixture was treated as described in Example 7. The yield of the unsaturated composition riched with 4,4'-divinylbiphenyl (DVBP) was 3.9 g (91.8% of theor.), mp 135–151° C. According to reversed phase chromatography, the content of components was as follows, wt-%: Monomer M1 (DVBP) 75, its unsaturated dimer 19, its insaturated trimer 5%, tetramers and higher oligomers 1%. Elemental analysis of the composition: Found, %: C 91.70, H 7.00. $M_n$ was 300 (number-average molecular weight of the composition was determined by measuring the thermal effects of condensation with a Hitachi-Perkin-Elmer osmometer, model 115).

Divinylaromatic Compositions of Higher Molecular Weight (Impoverished with Divinylaromatic Monomer)

Example 45

The mixture of 10.0030 g (0.03883 mole) of BHEPE, 0.010 g (0.1% of BHEPE weight) of 4-tert-butyl catechol, 0.1236 g (1.236% of BHEPE weight of 4.994 mmol/L) of TSA, and 120 mL of toluene was heated at the boiling temperature for 1 hour, 20 minutes. Water released during the dehydration was azeotroped from the system (~1.4 mL). Then, temperature was decreased down to 80° C. and the reaction mixture was kept at 80° C. additionally for 20 minutes. After treatment as described above, the product had high viscosity even at 140° C., softening temperature was 90–150° C. The content of components was as follows, wt-%: Monomer M1 (BVPE) ~5, its unsaturated oligomers according to formula (I) 95.

Example 46

The mixture of 10.000 g (0.03871 mole) of BHEPE, 0.010 g (0.1% of BHEPE weight) of 4-tert-butyl catechol, 0.0685 g (0.69% of BHEPE weight or 4.0 mmol/L) of TSA, and 90 mL of toluene was heated at the boiling temperature for 1 hour, 30 minutes. Water released during the dehydration was azeotroped from the system (~1.3 mL). Then, temperature was decreased down to 80° C. and the reaction mixture was kept at 80° C. additionally for 15 (the first sampling), 30 (the second sampling), 45 (the third sampling), 85 (the fourth sampling) minutes. After treatment as described above, the content of components in the composition was as follows, wt-%:

| No. of Samples (time, minutes) | M1 (BVPE), wt-% | unsaturated oligomers, wt-% |
|---|---|---|
| 1 (15) | 30 | 70 |
| 2 (30) | 25 | 75 |
| 3 (45) (high viscosity at 140° C.) | 16 | 84 |
| 4 (85) | 14 | 86 |

Example 47

The mixture of 180.00 g (0.6968 mole) of BHEPE, 0.1809 g (0.1% of BHEPE weight) of 4-tert-butyl catechol, 1.2325 g (0.685% of BHEPE weight of 3.99 mmol/L) of TSA, and 1440 mL of toluene was heated at the boiling temperature for 1 hour, 35 minutes. Water released during the dehydration was azeotroped from the system (24.5 mL). Then, temperature was decreased down to 80° C. and the reaction mixture was kept at 80° C. additionally for 35 minutes. After treatment as described above, the yield of the composition was 149 g, mp 35–45° C., $n_D^{60}$ 1.628, $n_D^{50}$ 1.634, $n_D^{40}$ 1.637, $n_D^{30}$ 1.640, $n_D^{25}$ 1.643, number-average molecular weight ($M_n$) 900 g/mole; the content of components in the composition was as follows, wt-%: M1 (BVPE) 20 and unsaturated oligomers described by formula (1) 80 (including its unsaturated dimer 15, unsaturated trimer 13, unsaturated tetramer 12, unsaturated pentamer 10, unsaturated hexamer 8, and higher homologues 22). Unsaturation of the composition was 0.53 mole double bonds/100 g of product.

The Shear Viscosity, by Rheogoniometer, at log g = 1.52 ($s^{-1}$): 0.84 Pas (80° C.); 0.20 Pas (100° C.); 0.015 Pas (140° C.); at log g = 0.178 ($s^{-1}$): ~15 Pas (80° C.) (where g is the shear rate).

For evaluation of this resin as a solventless heat and thermally stable matrix resin, unidirectional carbon fiber composites have been prepared with Russian unidirectional carbon fiber tape (commercially available under Russian trade name "LUP-01": density 1.7 g/cm$^3$, weight 35 g/m$^2$, number of fibers/10 cm 400 (warp), diameter of fiber 10–11 microns, porosity 3.5%, strength of 10 mm fiber 2.5 Gpa). Nine plies of the prepreg (1.8145 g) comprising 2.0 g of the resin, 0.010 g of benzoyl (BP) and 0.010 g of dicumyl (DCP) peroxides (thermoinitiators of radical polymerization) were stacked and heated in the temperature range 80–260° C. (° C./hrs: 80/2, 100/1, 120/1, 140/1, 160/2, 180/1, 220/1, 260/1) under specific pressure about 15 kgf/cm$^2$. The carbon fiber composites had the following flexural strength values, kgf/cm$^2$: (after final cure temperature 260° C./1 hour): 11,900–13,500@20° C., 5,000–7,000@250° C. and 4,800–5,000@320° C.; (after additional heating in air@320° C./2 hours): 4,900@320° C., 4,300@370° C., 1,800@400° C.

For the modification of epoxy resins aimed at improving their heat distortion temperature, the composition under consideration (C) was added to DGEBA. Tetrahydrophthalic (TA) and endic (EA) anhydrides were used as hardeners. Specific pressure for preparing fiberglass cloth laminates was about 1 kgf/cm$^2$. The conditions for preparing laminates was given in Table.

| | | Flexural Strength (kgf/cm$^2$) | | | |
|---|---|---|---|---|---|
| Reinforcement | Composition | 20° C. | 100° C. | 150° C. | 180° C. |
| 1. Fiberglass satin weave cloth, 6 plies | 1.5001 g of DGEBA (22 wt-% of epoxy groups) + 1.1442 g of EA + 0.4722 g of C + 0.0047 g of DCP (the cure schedule, ° C./hours: 120/1, 140/2, 140–180/0.5, 180/2, 220/1, 220–260/0.5, 260/1) | 7300 | 7000 | 5600 | 3600 |

-continued

| Reinforcement | Composition | Flexural Strength (kgf/cm$^2$) | | | |
|---|---|---|---|---|---|
| | | 20° C. | 100° C. | 150° C. | 180° C. |
| 2. Fiberglass satin weave cloth, 6 plies | 1.500 g of DGEBA (22 wt-% of epoxy groups) + 1.0605 g of TA + 0.3841 g of C + 0.0038 g of DCP (the cure schedule, ° C./hours: 120/1, 140/2, 140–180/0.5, 180/2, 220/1, 220–260/0.5, 260/1) | 8500 | 5000 | 1000 | — |
| The same | DGEBA + Anhydride | 5800 | 2300 | 400 | — |

Prepregs Preparation Capable of Long-Term Storage at RT

Example 48

The binder of the type A (binder A) is based on the Russian vinyl ester resin modified with divinylaromatic unsaturated composition obtained according to Example 39 (mp 82–86° C.) and the targeted additives.

A formulation (binder A) comprising 58.54 g of unsaturated polyester resin "NPS 609-21 M" (Russian trade name for the resin comprising the product of condensation of ethylene glycol with maleic and phthalic anhydrides mixed with dimethacrylate of triethylene glycol (as a reactive diluent), 2.95 g of epoxy resin ED-20 (Russian trade name for the epoxy resin derived from bisphenol A [DGEBA with 22 wt-% of epoxy groups]), 7.14 g of acrylamide, 30 g of divinylaromatic composition comprising 20 wt-% of BVPE (bis-(4-vinylphenyl)ether) and 80 wt-% of its unsaturated oligomers) (crosslinking agent), 0.14 g of benzoyl peroxide, 0.60 g of dicumyl peroxide, 0.050 g of Santoflex 13 (N-(1, 3-dimethyl-butyl)-N'-phenylphenylene-diamine-1,4, Monsanto Chem. Co. production) (antioxidant), and 0.57 g of Aerosil (fine divided silica powder as flow control agent) has been prepared.

For preparation of a unidirectional, resin-impregnated tape and fiberglass cloth commonly referred to as prepreg, a single ply of the carbon (glass) fabric was placed on a propylene film and then impregnation tape (cloth) with the binder—A (mp 45–60° C.) was performed at 70–90° C. using hot melt electric platen (0.7×0.52 m) made from carbon felt-fiber glass cloth laminate (prepregger). The binder's content in the prepreg was approximately 50% by weight.

The Cure Cycles and Properties of Composites

For fabrication of the glass cloth laminates, the prepregs prepared from the binder of the type A and fiberglass cloth of trademark "T-10-80" (6–8 plies) were stacked, heated and pressed under low specific pressure (1 kgf/cm$^2$) at 100–180° C. for 6–10 hours. For fabrication of carbon fiber composites, 9 plies of prepreg were pressed under specific pressure of 10 kgf/cm$^2$ and the same other conditions.

The fiberglass cloth laminates and carbon fiber composites had the following characteristics: thickness 1.40 and 0.95 mm, resin's content 30 and 30%, flexural strength (MPa): 600 and 900 at 20° C., 350 and 600 at 120° C., 250 and 500 at 150° C., 180 and 400 at 200° C., and very low value and 280 at 250° C., respectively.

Example 49

The binder of the type B (formulation B) is based on Zaitform resin modified with the divinylaromatic composition obtained according to Example 39 (mp 82–86° C., and the targeted additives. This formulation comprises the following ingredients: 30.0 g of the composition, 59.35 g of the Zaitform resin obtained according to Example 9, 3.00 g of epoxy resin (Russian trade name "ED-20" derived from bisphenol A, with 22.0 wt-% of epoxy groups and viscosity of 16 Pas), 7.00 g of methacrylamide, and 0.60 g of dicumyl peroxide, 0.05 g of Santoflex 13.

For fabrication of the glass cloth laminates, the prepregs prepared from formulation B, fiberglass cloth, or carbon fiber tape have been used at similar values of pressure (2 kgf/cm$^2$ for glass cloth laminates and 10 kgf/cm$^2$ for carbon fiber composites), the cure schedules include the increase in temperature from 100 to 300° C. for 8 to 11 hours.

The fiberglass cloth laminates and carbon fiber composites based on the binder B have the following characteristics: thickness 1.00 and 0.90 mm, flexural strength (MPa): 600 and 1200 at 20° C., 240 and 620 at 320° C., respectively, and additionally for carbon fiber composites: 520 at 350° C., and 250 at 400° C.

Example 50

According to the technical specification (TU 6–36–57–0–91) on Rolivsan MV-1, warranty concerning storage (shelf) time was 12 months of the date of preparation. For the purpose of increasing gelation time at RT, 0.0126 (0.5 wt-% of the resin weight) and 0.0125 g of dimethylformamide were added to 2.501 g of Rolivsan and 2.495 g of Zaitform resins, respectively, and two series of 10 samples of each modified resin were stored for a long time. Gelation time has been determined at 20, 80 and 150° C. in a month, a quarter, a year. The observation and the samples' testing for a long time (over 5 years) shows a slight increasing (approximately 10%) in viscosity of these samples and decreasing approximately 5–15%) in gelation time at 150° C. after storing for 3 years.

Example 51

Beads (grains) of styrene-BVPE resins of 5–10 microns' size) were obtained by bead (suspension) copolymerization of styrene with BVPE (10 wt-%) (crosslinking agent) in the system: styrene/water (1/20, in vol.), starch (0.5 wt-%) (stabilizer), isooctane (6 wt-%) (porogen), benzoyl peroxide (5 wt-%) (thermoinitiator) at stirring 9,000 revol./minute.

FIGS. 1 and 2 show SEC for a sample comprising a mixture of oligostyrene with the average molecular weight of 480 with benzene (microcolumn (0.5×300 mm), eluent was methylethylketone, the flow rate was 3 microliters/minute, the inlet pressure was 34 atm).

The polymerizable oligomers and resins of the present invention are shown in the examples to be available in different molecular weight ranges, generally referred to as middle or mid-range molecular weights (e.g., defined herein as about 200 to 500, preferably about 250 to 450), and middle or mid-range viscosity (e.g., defined herein as about 550 to 1050, preferably 600 to 1000 cps at 25° C.). The molecular weights referred to are number average molecular weights determined by measuring the thermal effects of condensation with a Hitachi-Perkin-Elmer osmometer (Model 115) with methodology was as published in Zaitsev, B. A. And Kiseleva, R. F., *Acta Polymerica*, 34 (10), pp.616–622, 1983. The viscosity was measured with a Heppler viscosimeter and Instron rheometer (e.g., "Rheotest-2," Vinogradov, G. V. and Malkin, A. Ya. *Rheology of Polymers,* Moscow, Chemistry Pubi., 1977, p. 120.

The content of vinyl endgroups referenced in the data and the examples herein (e.g., in compounds of the type $CH_2=CH-Ph-O-Ph-$) for the resins compositions was calculated on the basis of Size Exclusion Liquid Chromatography (SEC) data concerning the content and components of the composition. For example, the content of $CH_2=CH-$ groups (MWvinyl=27) in $CH_2=CH-Ph-O-Ph-CH=CH_2$ (MW1 M1=222), MW M2=308) and (MW M3=394) and (OL Mn~500) may be calculated according to the formulae, respectively:

wt.-% of $CH_2=CH-$ for M1=2×27×100/222=24.3%
wt.-% of $CH_2=CH-$ for M2=1×27×100/308=8.8%
wt.-% of $CH_2=CH-$ for M3=0×27×100/394=0.0%
wt.-% of $CH_2=CH-$ for OLigomers=1×27×100/500=5.4%

Hence, wt.-% of $CH_2=CH-$ for the composition comprising, wt.-% e.g.:

M1 30, M2 15, M3 25, and OL 30, is 10.2% (24.3×M1+ 8.8×M2+0×M3+5.4×OL, where σ(M1+M2+M3+ OL)=1 or 100%).

The content of ester endgroups, e.g., methacrylate groups $CH_2=C(CH_3)COO-$ ($M_{methacrylate}$=85) (in the compounds of the type $CH_2=C(CH_3)COO-(CH_3)CH-PhOPh-$ ...) for the composition (resin) was similarly calculated on the basis of SEC (Size Exclusion Liquid Chromatography) data concerning the content of the composition's components.

wt.-% of $CH_2=C(CH_3)COO-$ for M1=0×85×100/222= 0.0%
wt.-% of $CH_2=C(CH_3)COO-$ for M2=1×85×100/308= 27.6%
wt.-% of $CH_2=C(CH_3)COO-$ for M3=2×85×100/394= 43.2%
wt.-% of $CH_2=C(CH_3)COO-$ for OL=1×85×100/500= 17.0%

Hence, wt.-% of $CH_2=C(CH_3)COO-$ for the composition comprising, wt.-% e.g.:

M1 30, M2 15, M3 25, and OL 30, is 20% (0×M1+27.6× M2+43.2×M3+17×OL, where σ(M1+M2+M3+OL)=1 or 100%).

Quantitative Analysis of Phenolic Impurities in Bis-[4-(1-hydroxyethyl)phenyl] Ether (BHEPE) Produced on a Pilot Plant.

Photometric method of the determination of phenols was used and tailored for quantitative analysis of phenolic impurities in several batches of bis-[4-(1-hydroxyethyl)phenyl] ether (BHEPE) produced on a pilot plant. The method was based on the formation of the color azo compounds as a result of azo coupling of phenols with diazotized p-nitroaniline (Korenman I. M. Photometric Analysis. Methods for the Determination of Organic Compounds. Moscow, Chemistry Publ., 1970, p. 43 (in Russian); Smith G., King D. Analyst 1964, 89, 305,312; 1965, 90, 55). The analysis was performed with photoelectrical colorimeter "PhEK-56M" for 35 minutes. As pattern for plotting the calibration curve was used sublimated p-cresol. Optical density of azo compounds was measured in the system of ethyl alcohol : water=1:4 at $\lambda_{max}$=490±10 nm in the cell of 50 mm. The accuracy of the analysis was 0.02%. The results of the analysis of the different samples of BHEPE are listed in Table.

TABLE

The results of the photometric analysis of phenolic impurities in bis-[4-(1-hydroxyethyl)phenyl]ether (BHEPE) produced on a pilot plant by the hydrogenation of bis-(4-acetylphenyl) ether with successive purification of the diol by recrystallization from benzene.

| Batch No. | Characateristics of the diol's batch | Content of phenolic impurities, wt.-% |
|---|---|---|
| 1. | Industrial BHEPE (without additional purification), mp 82–84° C. | 1.32, 1.52, 1.43 |
| 2. | Industrial BHEPE (without additinal purification), mp 83–85° C. | 0.34, 0.52, 0.87 |
| 3. | Industrial BHEPE (recrystallized from toluene), mp 85–86° C. | 0.18, 0.20 |
| 4. | Industrial BHEPE (recrystallized from aqueous ethyl alcohol), mp 86° C. | 0.20, 0.23 |
| 5. | Industrial BHEPE (after alkali water-alcohol purification), mp 89–91° C. | 0.10, 0.13 |
| 6. | Industrial BHEPE (after alkali water-alcohol purification), mp 89–91° C. | 0.09, 0.13 |
| 7. | Industrial BHEPE (after alkali water-alcohol purification and recrystallization from toluene), mp 90–91° C. | 0.06, 0.07, 0.09 |

Synthesis of Zaitform resins based on the transformations bis-[4-(1-hydroxyethyl) phenyl] ether and methacrylic acid was carried out according to Examples 52 and 53.

Example 52

The mole ratio Diol (D(: methacrylic acid (MAA)=1:1.5. The mixture of 100.00 g (0.3871 mole) of the purified BHEPE 0.200 g (0.20% of BHEPE weight) of 4-tert-butyl catechol, 0.4003 g (0.40% of BHEPE weight or 1.830 mmol/L) of TSA, 49.2 mL (49.94 g, or 0.5801 mole) of the freshly-distilled methacrylic acid, and 1000 mL of toluene was heated at the boiling temperature for 1 hour 40 min. Water released during the dehydration was azeotroped from the system (12.1 mL). Then the temperature was decreased to 70° C., 0.4008 g of the extra-amount of TSA was added to the reaction mixture, and the reaction mixture was maintained and stirred at 70° C. for 0.5 hour. After treatment as described above, the yield was 104 g, $n_D$20 1.591. The content of components according SEC was as follows, wt %: Monomer M1 (BVPE) 12, Monomer 2 (monoester) 29, Monomer 3 (diester) 24, and an unsaturated oligomer (mixture) which could be described by the formula (1) 35.

Example 53

The mole ratio Diol (D): methacrylic acid (MAA)=1:1.5. The mixture of 100.05 g (0.3871 mole) of the purified BIEPE 0.202 g (0.20% of BHEPE weight) of 4-tert-butyl catechol, 0.2994 g (0.30% of BHEPE weight or 1.830 mmol/L) of TSA, 49.2 mL (49.94 g, or 0.5801 mole) of the freshly-distilled methacrylic acid, and 1000 mL of toluene was heated at the boiling temperature for 2 hours. Water released during the dehydration was azeotroped from the system (12.0 mL). The temperature was decreased to 70° C., 0.3012 g of the extra-amount of TSA was added to the reaction mixture, and the reaction mixture was maintained and stirred at 70° C. for 0.5 hour. After treatment as described above, the yield was 106 g, $n_D$20 1.587. The content of components according SEC was as follows, wt %:

Monomer M1 (BVPE) 14, Monomer 2 (monoester) 32, Monomer 3 (diester) 26, unsaturated oligomers (mixture) which could be described by the formula (1) 28.

The standard alkali buffer solution having pH=12 was prepared from the solution of 0.1 mole/L NaOH and 0.1 mole/L $NH_2CH_2COOH$.

The specimens of glass cloth laminates have been prepared on the basis of the glass fabric (Russian trade name "T-10-80" (unannealed). Five plies, size 5×2.5 cm were stacked, heated, and pressed under specific pressure of about 1.0 $kgf/cm^2$. The cure schedule was ° C./hrs: 150/1, (150–160/15 min, 160–180/30 min, 180/2, 180–200/30 min, 200/1, 200–220/30 min, 220/1, 220–250/30 min, 250/1, 250–260/15 min, 260/1. The thickness of the laminates' specimens was 0.90 to 1.00 mm.

The effect of the exposure of alkali buffer solution (pH=12) at room and boiling (>100° C.) temperature on flexural strength of the specimens of clear castings and glass cloth laminates based on the cured Zaitform resins.

down to gaseous and volatile substances at a higher temperature of pyrolysis (>350° C.) and especially under reduced pressures 0.01 to 600 mm Hg. Hence, cooking values for the cured Rolivsan and Zaitform resins which have highly crosslinked polymer networks are extremely low (5–15%) as compared to phenol-formaldehyde, aromatic polyimide, and other thermostable resins. Another unusual level of performance of the crosslinked polymers formed by curing Zaitform resins is their ability of transition to the gaseous state without melting.

These two unusual properties of these resins are quite important for developing and advancing my new revolutionary ideas for up-to-date printing technology.

There is a significant problem in the development of modem technology in printing industry use of LaserGraver Systems (Computer-to-plate) because of the absence of materials capable of providing sufficiently high resolution.

The advantages of the use of Rolivsan and/or Zeitsev resins in this technology can be seen from the following type of requirements or standards sought in the industry.

| Specimen No. | Exposure, temp./time | Laminates | | Clear Castings | | Increase in weight, wt-% |
|---|---|---|---|---|---|---|
| | | $s_F$ 20 C., $kgf/cm^2$ | $s_F$ 250 C., $kgf/cm^2$ | $s_F$ 20 C., $kgf/cm^2$ | $s_F$ 250 C., $kgf/cm^2$ | |
| 1 Example 52 | 0 | 6570 5840 6130 average: 6200 | 2970 2720 average: 2800 | 710 670 880 average: 750 | 530 570 470 average: 520 | — |
| 1a | RT/105 days + >100° C./144 hrs | 4460 3500 4130 average: 4030 | 3140 3320 average: 3230 | 640 670 660 average: 660 | 310 290 average: 300 | 2.2 |
| 2 Example 53 | 0 | 6720 5600 6400 average: 6200 | 3790 3130 average: 3460 | — | — | — |
| 2a | RT/105 days + >100° C./144 hrs | 3360 3060 2430 average: 2950 | 2580 2630 average: 2600 | — | — | 0.5 |

It may be seen from the Table that, despite extremely severe conditions of the accelerated againg test(which may be compared with testing for several decades at the average outdoor temperature range 10 to 20° C.), flexural strenth strength retention for glass cloth laminates measured at 20° C. and 250 ° C. are 48–65 and 75–115% of the initial values, respectively. Even the more impressed test results have been obtained for clear castings: 88 (at 20 C) and 58% (at 250 C) of flexural strength retention.

It is obvious that Zaitform resins, with much more alkali resistant units (compared to diphenyl ether unit), such as diphenylmethane or biphenyl units, could demonstrate still more impressive results.

A. Zaitform resins are capable of exerting revolutionary influence on the advancement of high technology to printing industries It has been established by experimentation that the polymer network of the both the cured Rolivsan and the cured Zaitform resins is capable of pyrolytic splitting resulting in the formation of fusible, soluble and curable oligomers at comparatively moderate temperature (320–340° C.) of the pyrolysis. This network can be fully and rapidly broken- Computer-to-plate, Direct Imaging, LaserGraver Systems, DAYLIGHT OPERATION, DRY, NO-CHEMICAL PROCESS, 2540 dpi RESOLUTION, 180 lpi SCREEN RULING, Master films, offset plates. LaserGraver machines utilize an advanced engraving imaging technology that enables to produce both master films and offset plates with 2540 dpi resolution in single-stage, no-chemical process.

Direct dry image setting master films are engraved on inexpensive silverless film coated with thin black resin layer. The image is formed by ablation of the coating while transparent film base remains untouched. The coating has a high optical density of 4.5 Dlog, thus providing high contrast for the film. A small size of laser spot (up to 10 mm) provides true 2540 dpi resolution up to 180 lpi screen ruling for color separation. As the imaging process does not require any chemicals, laser engraving in its essence is a waterless and single-stage process.

LaserGraver is controlled by PC-based Level 2 software RIP and supports all features commonly found in imagesetters, as in Direct Imaging Computer-to-Plate systems. The most important advantage of engraving technology is in realization of direct single-stage dry Computer-to-Plate processing.

The same ablation principle is used to make different types of offset plates: aluminum-based plates for large runs and color printing, polyester plates for medium runs and black-and-white printing and resin-coated paper plates for small orders. LaserGraver actually substitutes a whole equipment set for traditional offset prepress: and imagesetter, film processing equipment, UV plate copying unit and a plate processor, and does it with no sacrifice of quality. With LaserGraver machines, it is asserted that one can use any desktop publishing software for Windows and Apple. The LaserGraver may be serviced by one operator.

LaserGraver may be used with asserted new standards of quality in rubber stamp manufacturing. This high power laser machine engraves rubber sheet with the finest yet powerful light beam directly, producing deep gravure with extremely small and accurate elements. The rubber needs no processing after engraving and can be cut in individual pieces, pasted to the stamp and delivered to customer immediately.

LaserGraver opens a new possibilities in rubber stamp layout design. Now you can use halftoned photos, extremely fine type (1–2 points), complicated pattern like those found in bank notes. It is possible to define a slope angle of printing elements profile in order to increase stamp lifetime and to avoid image distortion in case of inaccurate stamping. The quality and precision of manufacturing process makes faking of the stamps almost impossible. With its 2032 dpi resolution (2540 dpi resolution optional), LaserGraver provides the quality of imaging close to that of imagesetter. LaserGraver is a desktop unit completely controlled via software. It makes about 12 rubber stamps per hour. From the viewpoint of software, it behave like PostScript printer or imagesetter. The soft ware PC-based RIP gives access to all features of both PC and Macintosh desktop publishing software.

LaserGraver could also be used in so called imagesetter mode. In this mode, it engraves special black resin coated film directly producing master films of imagesetter quality. The film needs no developing and costs much less than ordinary photosensitive film. Its optical density is as high as 4.5 Dlog.

The quality is sufficient for color separations with up to 133 lpi screen ruling. In fact it is enough for many purposes such as business card manufacturing, low-run offset printing, silk screen printing photopolymer platemaking, etc. With LaserGraver, quality films could be made in-house. Actually, the machine is ideal "all-in-one solution for small enterprises, eliminating all wet and darkroom process.

Amongst the producers of the LaserGraver types of machines are "TRODAT" (Austria), "CASLON", "BAASEL-SCHEEL LASERGRAPHICS GmbH" (Germany); materials for laser engraving are produced by Du Pont and BASF. However, the conventional materials provide the resolution only 120–133 lpi.

ZAITFORM COATING on PHENOL-FORMALDEHYDE RESINS ARTICLES provide a RESOLUTION of 320 lpi. This implies that the resins can be used for obtaining the printing materials of the most high quality.

Example 54. The formulation comprising 0.900 g of Zaitform resin (obtained according to Example 52), and Rolivsan MV-1 resin, 0.01 g dicumyl peroxide, and 0.05–0.09 g of carbon black was prepared at 50–120° C. and stirring. The formulation was heated to 100–140° C. and was applied on a hot polymer roller made from phenol-formaldehyde molding powder. The thickness of the Zaitform layer (cover) was 30–500 microns. The following cure schedule was used (° C./hours): 140/1, 140–170/0.5, 170/2, 170–200/0.5, 200/4. Engraving was performed with LaserGraver SP45 (ALPHA Research& Manufacturing Co., Moscow, Russia):

Resolution 508, 1016, 1422, 2032, 2540 dpi
Laser spot size: 10–80 micron
Min. dot size: 10 micron
Imaging time (for 2540 resolution): A4 15 min
Laser type (wavelength): solid-state YAG: Nd (1.06 microm)
Input data format : PostScript, PCX
Operation environment: daylight, prepress area
The resolution for the Zaitform coat filled with carbon black has attained to a top value (320 lpi).

B. Glassfiber reinforcing bars based on Zaitform resins in structural concrete applications It has been shown that both Rolivsan and Zaitform resins exhibited excellent chemical resistance to the most aggressive reagent, including any solvents, strong acids, alkalis, and even hot solutions of hydrofluoric acid (HF) and hydrazine. Thus, they have a great potential to resist chemical attack from exposure to both strongly acidic and highly alkaline agents and media.

These properties permit an expectation of the utility of the resins in fabricating glass-fiber-reinforced composites which could replace corrosion-prone, steel-reinforcements in structural concrete applications. Such polymers could also be useful in producing corrosion-resistant coatings for a broad range of reinforcing media that could be used in concrete (e.g., steel, glass, plastics, and composites of these materials).

It is especially important, because reinforcing rods or bars manufactured on the basis of the conventional vinylester or unsaturated polyester resins and used currently as commercially-available reinforcements in structural concrete applications, are unable to withstand long-term exposure to highly alkaline absorbed water in concrete (e.g., pH=~12).

For evaluating Zaitform resins as binders in reinforcing rods (bars) for use as alkali resistant materials, accelerated aging test have been carried out. For this purpose, the investigation of the dependence of the flexure strength of cured Zaitform resins, (specimens of glass cloth laminates and clear castings) on exposure to alkali buffer solution both at room temperature (RT) and boiling temperature has been performed.

What is claimed is:

1. A composition consisting essentially of at least 99.3% mole basis of an ethylenically unsaturated compound of the formula:

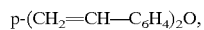
p-(CH$_2$=CH—C$_6$H$_4$)$_2$O, or

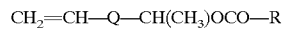
CH$_2$=CH—Q—CH(CH$_3$)OCO—R wherein Q is a diaryl group comprising two aryl groups linked together directly or bridged by an oxygen atom, sulfur atom or methine group, and R is hydrogen or an alkyl group, and said ethylenically unsaturated compound comprises less than 0.7% mole basis of monoaryl hydroxy compounds.

2. A composition consisting essentially of at least 99% mole basis of an ethylenically unsaturated compound of the formula:

p-(CH$_2$=CH—C$_6$H$_4$)$_2$O, or

CH$_2$=CH—Ar—O—Ar—CH(CH$_3$)OCO—R, wherein each Ar is an aromatic group, and

R is hydrogen or an alkyl group, wherein said ethylenically unsaturated compound has less than 1% mol basis of monoaryl phenolic compounds.

3. The composition of claim 1 wherein R comprises a vinyl group.

4. The composition of claim 1 wherein R comprises an allyl group.

5. The composition of claim 1 wherein R comprises an ethylenically unsaturated group.

6. The composition of claim 1 wherein each aryl group is a phenyl group.

7. The composition of claim 2 wherein Ar is a phenyl group.

8. The composition of claim 2 wherein O is selected from the group consisting of phenyl, naphthyl and furyl groups.

9. The composition of claim 2 wherein Ar is selected from the group consisting of phenyl, naphthyl and furyl groups.

10. The composition of claim 2 wherein the ethylenically unsaturated compound has the formula:

p-(CH$_2$=CH—C$_6$H$_4$)$_2$O, or

CH$_2$=CH—C$_6$H$_4$—O—Ar—CH(CH$_3$)OCO—R, wherein Ar is an aromatic group, and

R is hydrogen or an alkyl group, wherein said ethylenically unsaturated compound has less than 1% mol basis of monoaryl phenolic compounds.

11. The composition of claim 10 wherein Ar is a phenyl group.

12. The composition of claim 1 wherein the composition is in a solution.

13. The composition of claim 2 wherein the composition is in a solution.

14. The composition of claim 3 wherein the composition is in a solution.

15. The composition of claim 4 wherein the composition is in a solution.

16. The composition of claim 5 wherein the composition is in a solution.

17. The composition of claims 6 wherein the composition is in a solution.

18. The composition of claim 7 wherein the composition is in a solution.

19. The composition of claim 8 wherein the composition is in a solution.

20. The composition of claim 9 wherein the composition is in a solution.

21. The composition of claim 10 wherein the composition is in a solution.

22. The composition of claim 11 wherein the composition is in a solution.

* * * * *